(12) United States Patent
Metzger

(10) Patent No.: US 11,946,921 B2
(45) Date of Patent: Apr. 2, 2024

(54) SYSTEMS AND METHODS FOR IMPROVING THE PERFORMANCE OF ENVIRONMENTAL MEASUREMENTS

(71) Applicant: Stefan Metzger, Boulder, CO (US)

(72) Inventor: Stefan Metzger, Boulder, CO (US)

(*) Notice: Subject to any disclaimer, the term of this patent is extended or adjusted under 35 U.S.C. 154(b) by 331 days.

(21) Appl. No.: 16/679,200

(22) Filed: Nov. 9, 2019

(65) Prior Publication Data

US 2020/0151522 A1 May 14, 2020

Related U.S. Application Data

(60) Provisional application No. 62/758,269, filed on Nov. 9, 2018.

(51) Int. Cl.
| | | |
|---|---|---|
| *G01N 33/24* | (2006.01) | |
| *G06F 17/15* | (2006.01) | |
| *G06F 18/25* | (2023.01) | |
| *G06N 20/00* | (2019.01) | |
| *G06V 20/13* | (2022.01) | |

(52) U.S. Cl.
CPC .......... *G01N 33/24* (2013.01); *G06F 17/15* (2013.01); *G06F 18/251* (2023.01); *G06N 20/00* (2019.01); *G06V 20/13* (2022.01)

(58) Field of Classification Search
CPC ....... G06K 9/6289; G01N 33/24; G06F 17/15
USPC .......................................................... 702/1
See application file for complete search history.

(56) References Cited

U.S. PATENT DOCUMENTS

| | | |
|---|---|---|
| 7,953,558 B2 | 5/2011 | Burba et al. |
| 8,595,020 B2 | 11/2013 | Marino |
| 2018/0262918 A1* | 9/2018 | Zhao .................... H04B 7/0695 |
| 2018/0275658 A1* | 9/2018 | Iandola ............... G06F 18/2148 |
| 2020/0309960 A1* | 10/2020 | Arditi ..................... G01S 19/45 |
| 2021/0289723 A1* | 9/2021 | Mewes ................ A01G 25/167 |
| 2022/0276625 A1* | 9/2022 | Metzger ................. G05B 15/02 |

(Continued)

OTHER PUBLICATIONS

Desjardins, R. L., Worth, D. E., Pattey, E., VanderZaag, A., Srinivasan, R., Mauder, M., Worthy, D., Sweeney, C., and Metzger, S.: The challenge of reconciling bottom-up agricultural methane emissions inventories with top-down measurements, Agric. For. Meteorol., 248, 48-59, doi:10.1016/j.agrformet.2017.09.003, 2018. Elsevier: US/Netherlands (Published online).

(Continued)

*Primary Examiner* — Michael P Nghiem

(57) ABSTRACT

Methods and systems for enhancing environmental response data from natural and/or anthropogenic environments can use physical laws and data science principles to combine the information contained in environmental response input data and at least two independent types of environmental driver input data to produce environmental response data that has been enhanced from the environmental response input data in at least one of the following ways:

the environmental response output data has improved accuracy;

the environmental response output data has improved precision;

the environmental response output data comprises a greater number of times;

the environmental response output data comprises a greater number of locations in one-dimensional, two-dimensional, or three-dimensional space.

16 Claims, 14 Drawing Sheets

(56) References Cited

U.S. PATENT DOCUMENTS

2022/0308260 A1* 9/2022 Huang .................. G01V 99/00
2023/0066501 A1* 3/2023 Jonietz ................ G08G 1/0112

OTHER PUBLICATIONS

Kohnert, K., Serafimovich, A., Metzger, S., Hartmann, J., and Sachs, T.: Strong geologic methane emissions from discontinuous terrestrial permafrost in the Mackenzie Delta, Canada, Scientific Reports, 7, 5828, doi:10.1038/s41598-017-05783-2, 2017. Nature: UK (Published online).

Kohnert, K., Juhls, B., Muster, S., Antonova, S., Serafimovich, A., Metzger, S., Hartmann, J., and Sachs, T.: Toward understanding the contribution of waterbodies to the methane emissions of a permafrost landscape on a regional scale—A case study from the Mackenzie Delta, Canada, Global Change Biol., 24, 3976-3989, doi:10.1111/gcb.14289, 2018. Wiley US (Published online).

Metzger, S.: Applicability of weight-shift microlight aircraft for measuring the turbulent exchange above complex terrain, Doctoral thesis, Faculty of Biology, Chemistry and Geosciences, University of Bayreuth, Bayreuth, 131 pp., 2013. Germany.

Metzger, S., Junkermann, W., Mauder, M., Butterbach-Bahl, K., Trancón y Widemann, B., Neidl, F., Schäfer, K., Wieneke, S., Zheng, X. H., Schmid, H. P., and Foken, T.: Spatially explicit regionalization of airborne flux measurements using environmental response functions, Biogeosciences, 10, 2193-2217, doi:10.5194/bg-10-2193-2013, 2013. Copernicus Publications, Germany.

Metzger, S., Durden, D., Sturtevant, C., Luo, H., Pingintha-Durden, N., Sachs, T., Serafimovich, A., Hartmann, J., Li, J., Xu, K., and Desai, A. R.: eddy4R 0.2.0: a DevOps model for community-extensible processing and analysis of eddy-covariance data based on R, Git, Docker, and HDF5, Geosci. Model Dev., 10, 3189-3206, doi:10.5194/gmd-10-3189-2017, 2017. Copernicus Publications, Germany.

Metzger, S.: Surface-atmosphere exchange in a box: Making the control volume a suitable representation for in-situ observations, Agric. For. Meteorol., 255, 68-80, doi:10.1016/j.agrformet.2017.08.037, 2018a. Elsevier: US/Netherlands (Published online).

Metzger, S.: Surface-atmosphere exchange in a box [popular science article], https://sciencetrends.com/surface-atmosphere-exchange-in-a-box/, doi:10.13140/RG.2.2.33535.51362, 2018b. US.

Serafimovich, A., Metzger, S., Hartmann, J., Kohnert, K., Zona, D., and Sachs, T.: Upscaling surface energy fluxes over the North Slope of Alaska using airborne eddy-covariance measurements and environmental response functions, Atmos. Chem. Phys., 18, 10007-10023, doi:10.5194/acp-18-10007-2018, 2018b. Copernicus Publications, Germany.

Sühring, M., Metzger, S., Xu, K., Durden, D., and Desai, A.: Trade-offs in flux disaggregation: a large-eddy simulation study, Boundary Layer Meteorol., 170, 69-93, doi:10.1007/s10546-018-0387-x, 2018. US.

Vaughan, A. R., Lee, J. D., Misztal, P. K., Metzger, S., Shaw, M. D., Lewis, A. C., Purvis, R. M., Carslaw, D. C., Goldstein, A. H., Hewitt, C. N., Davison, B., Beevers, S. D., and Karl, T. G.: Spatially resolved flux measurements of NOx from London suggest significantly higher emissions than predicted by inventories, Faraday Discuss., 189, 455-472, doi:10.1039/c5fd00170f, 2016. Royal Society of Chemistry UK.

Vaughan, A. R., Lee, J. D., Shaw, M. D., Misztal, P. K., Metzger, S., Vieno, M., Davison, B., Karl, T. G., Carpenter, L. J., Lewis, A. C., Purvis, R. M., Goldstein, A. H., and Hewitt, C. N.: VOC emission rates over London and South East England obtained by airborne eddy covariance, Faraday Discuss., 200, 599-620, doi:10.1039/c7fd00002b, 2017. Royal Society of Chemistry UK.

Xu, K., Metzger, S., and Desai, A. R.: Upscaling tower-observed turbulent exchange at fine spatio-temporal resolution using environmental response functions, Agric. For. Meteorol., 232, 10-22, doi:10.1016/j.agrformet.2016.07.019, 2017. Elsevier: US/Netherlands (Published online).

Xu, K., Metzger, S., and Desai, A. R.: Surface-atmosphere exchange in a box: Space-time resolved storage and net vertical fluxes from tower-based eddy covariance, Agric. For. Meteorol., 255, 81-91, doi:10.1016/j.agrformet.2017.10.011, 2018. Elsevier: US/Netherlands (Published online).

\* cited by examiner

| Full $H_2O$ flux conservation equation for single unit cube with side length $S_R$ (Fig. 7) | 0610 |

↓ 0620

Space ensembling over extent $S_E$ using interval $S_I$ cancels horizontal terms — 0621

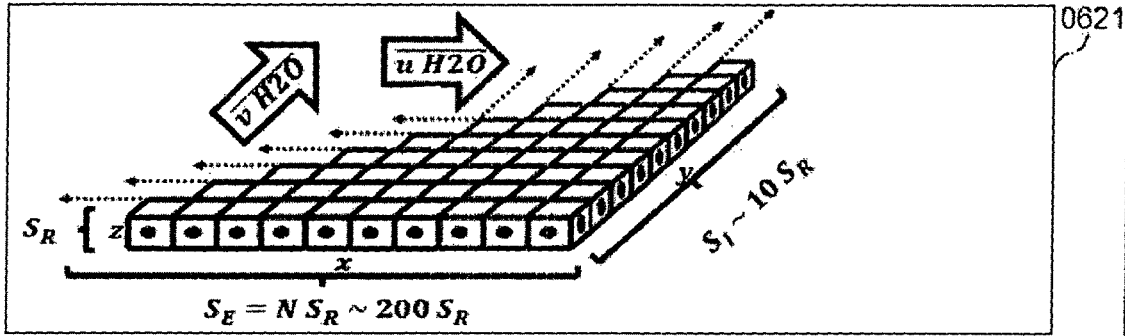

$S_E = N S_R \sim 200 S_R$ $H_2O$ transport through along-wind walls    $H_2O$ transport through cross-wind walls — 0622

$$\int_0^{S_R}\left[\frac{1}{S_E^2}\int_0^{S_E}\int_0^{S_E}\frac{\partial \overline{u\,H2O}}{\partial x}\,dxdy\right]dz \;+\; \int_0^{S_R}\left[\frac{1}{S_E^2}\int_0^{S_E}\int_0^{S_E}\frac{\partial \overline{v\,H2O}}{\partial y}\,dxdy\right]dz \;\to\; 0$$

Tolerance $T_{hor}$ of cancelling horizontal terms as function of their fractional area $A$ — 0623

$$T_{hor} \propto \frac{A_{hor,xz}+A_{hor,yz}}{A_{top,xy}} = \frac{(2+2)N}{N^2} = \frac{4}{N}\,;\; N=200 \Rightarrow T_{hor} \propto 2\%$$

↓ 0630

Space ensembling cancels horizontal-compensatory fluxes from remaining terms — 0631

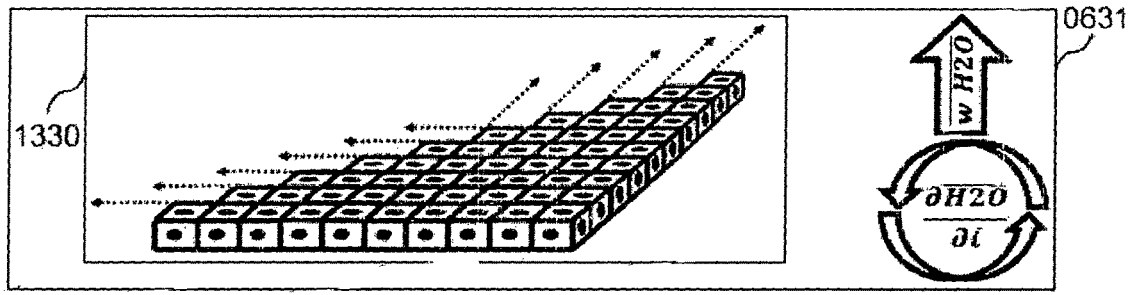

1330

$H_2O$ accumulation in volume    $H_2O$ transport through ceiling — 0632

$$f_{H2O} \to \int_0^{S_R}\left[\frac{1}{S_E^2}\int_0^{S_E}\int_0^{S_E}\frac{\partial \overline{H2O}}{\partial t}\,dxdy\right]dz \;+\; \frac{1}{S_E^2}\int_0^{S_E}\int_0^{S_E}\overline{w\,H2O}(S_R)\,dxdy$$

Tolerance $T_{comp}$ of cancelling horizontal-compensatory fluxes — 0633

$$T_{comp} \propto \frac{1}{\sqrt{N^2}} = \frac{1}{N}\,;\; N=200 \Rightarrow T_{comp} \propto 0.5\%$$

Fig. 6

SYSTEMS AND METHODS FOR IMPROVING THE PERFORMANCE OF ENVIRONMENTAL MEASUREMENTS

This patent application claims benefit of U.S. Provisional Patent Application Ser. No. 62/758,269 filed 9 Nov. 2018, the entire disclosure of which are incorporated by reference herein.

FIELD OF INVENTION

The present invention relates to scientific measurements. More specifically, the present invention relates to systems and methods that combine information from multiple instruments to improve the performance of a scientific measurement. Examples of these improvements to scientific measurements can include (a) improving the accuracy and/or precision of a measurement by reducing systematic errors and/or random errors and (b) increasing the resolution, extent, and/or coverage of a measurement in space and/or time.

BACKGROUND

It can be difficult and expensive to measure certain physical phenomena directly at a sufficient number of locations (i.e., space resolution, space extent and space coverage) and/or with sufficient repetition rate and duration (i.e., time resolution, time extent and time coverage) to make scientific computations at the desired accuracy, precision, random error, systematic error, and/or resolution, extent and coverage in space and/or time. This is because some types of environmental measurements require expensive instrumentation, instruments that are difficult to deploy at all the required physical locations, repetition rate and duration, and/or instrumentation can affect the environment being measured. For example, the instrumentation to measure momentum, energy and mass fluxes in a fluid is complex, expensive, and invasive of the environment being measured.

Other types of physical phenomena can be measured relatively easily, quickly, inexpensively, accurately, precisely, and/or at a high resolution, extent and coverage in space and/or time. For example, temperature is relatively easy and inexpensive to measure, and can even be measured remotely since a radiating body will give off a specific electromagnetic spectral signature. That's how we can measure the temperatures of distant astronomical bodies. If it were possible to relate information from inexpensive measurements to information from more expensive measurements, one could use the inexpensive data to improve the accuracy, precision and/or resolution, extent and coverage in space and/or time of the expensive data.

Similarly, the time response of some physical phenomena and/or some scientific instruments is much faster than the time response for other physical phenomena and/or instruments. For example, surface temperature can change faster than internal temperature as a result of the thermal mass (heat capacitance) of an object. Thus, high-frequency (i.e., time resolution) measurement of the surface of an object can be used to determine internal temperature as well as being able to facilitate the modeling of the internal heat flux.

Furthermore, instruments can produce systematic and/or random errors as a result of damage, wear, aging, etc., and scientific computations can produce systematic and/or random errors as a result of limited resolution, extent and/or coverage in space and/or time of the measurements. By relating measurements from multiple instruments using innovative systems and/or methods it may be possible to compensate for such systematic and/or random errors.

In summary, the goal is a system/method that measures physical phenomena in the most effective and cost-efficient way. This is achieved through combining complementary information from multiple instrument types to optimize joint measurement performance, i.e., accuracy, precision and/or resolution, extent and coverage in space and/or time.

BRIEF DESCRIPTION OF THE DRAWINGS

The present disclosure is described in conjunction with the appended figures in which:

FIG. 6 shows an example of how a physical constraint shown in FIG. 7 can be realized by reducing the $H_2O$ flux conservation equation in FIG. 7 to two fully quantifiable differential equation terms by means of space-time deconvolution and subsequent ensembling;

Figure 1:
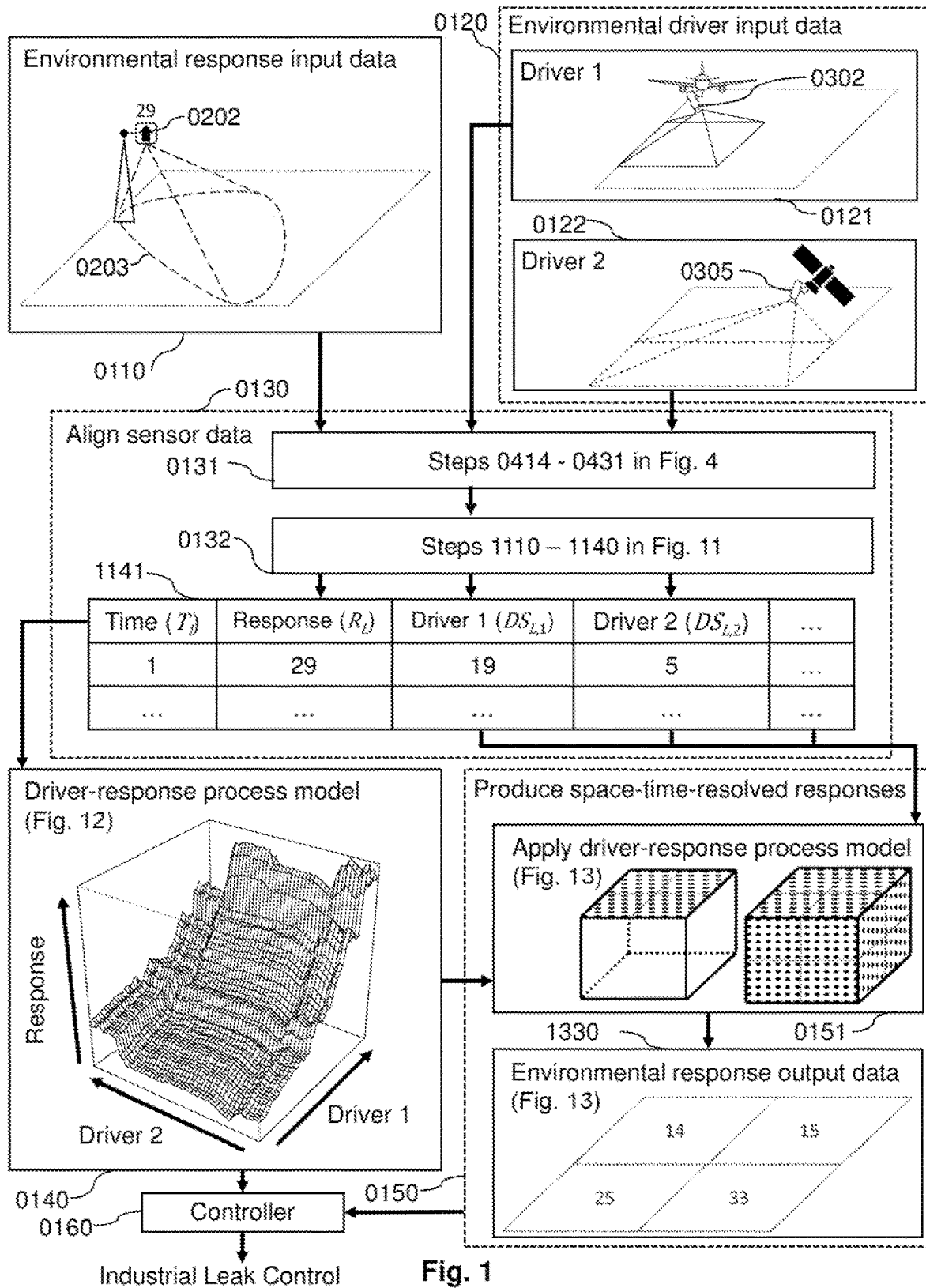
FIG. 1 provides a high-level overview of a processor for combining environmental response input data 0110 and environmental driver input data 0120 to generate environmental response output data 1330 having an improved accuracy, precision, resolution, extent and/or coverage in space and/or time compared to the environmental response input data 0110.

It should be understood that the drawings are not necessarily to scale. In certain instances, details that are not necessary for an understanding of the invention or that render other details difficult to perceive may have been omitted. It should be understood that the invention is not necessarily limited to the particular embodiments illustrated herein.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It should be understood that various changes could be made in the function and arrangement of elements without departing from the spirit and scope as set forth in the appended claims.

Specific details are given in the following description to provide a thorough understanding of the embodiments. However, it will be understood by one of ordinary skill in the art that the embodiments may be practiced without these specific details. For example, those skilled in the art will know that different data sources, data sets, instrumentation, measurements, physical parameters, process steps, execution order, physical models, and mathematical models, may be substituted.

1. Definitions

In one embodiment, the system and/or method can be used for improving the accuracy of a measurement. For purposes of this document and the appended claims, accuracy is defined as the closeness of the measurements to a reference value.

In this disclosure and the appended claims, the system or method could be used for improving the precision of a measurement. For purposes of this document and the appended claims, precision is defined as the closeness of measurements to each other.

In this disclosure and the appended claims, the system or method could be used for reducing systematic measurement errors. For purposes of this document and the appended claims, the term systematic error is defined as an accuracy error.

In this disclosure and the appended claims, the system or method could be used for reducing random measurement errors. For purposes of this document and the appended claims, the term random error is defined as a precision error.

In this disclosure and the appended claims, the system or method could be used for improving space resolution. For purposes of this document and the appended claims, the term space resolution is defined as the smallest distance, area or volume rendered by a measurement and/or set of data.

In this disclosure and the appended claims, the system or method could be used for improving space extent. For purposes of this document and the appended claims, the term space extent is defined as the largest distance, area or volume encompassed by a measurement and/or set of data.

In this disclosure and the appended claims, the system or method could be used for improving space coverage. For purposes of this document and the appended claims, the term space coverage is defined as the degree to which a measurement and/or set of data populates a space extent.

In this disclosure and the appended claims, the system or method could be used for improving time resolution. For purposes of this document and the appended claims, the term time resolution is defined as the shortest duration rendered by a measurement and/or set of data.

In this disclosure and the appended claims, the system or method could be used for improving time extent. For purposes of this document and the appended claims, the term time extent is defined as the longest duration encompassed by a measurement and/or set of data.

In this disclosure and the appended claims, the system or method could be used for improving time coverage. For purposes of this document and the appended claims, the term time coverage is defined as the degree to which a measurement and/or set of data populates a time extent.

In this disclosure and the appended claims, the system or method could be used for improving the performance of a measurement. For purposes of this document and the appended claims, the term performance is defined as any one or more of accuracy, precision, random error, systematic error, space resolution, space extent, space coverage, time resolution, time extent, time coverage.

For purposes of this document and the appended claims, the term coordinate representation is defined as the use of one or more variables to uniquely determine the location of points or other geometric shapes such as lines, areas or volumes.

For purposes of this document and the appended claims, the term Eulerian is defined as a coordinate representation that registers objects as a function of time and location, along a symmetric, regular and static line (1-dimensional), plane (2-dimensional, e.g. flat Eulerian surface), and/or volume (3-dimensional).

For purposes of this document and the appended claims, the term Lagrangian is defined as a coordinate representation that registers objects by following their trajectory as a function of time, along an asymmetric, irregular and transient 1-dimensional line, 2dimensional plane, and/or 3-dimensional volume. Aggregating the 3-dimensional trajectories of a multitude of objects from their joint destination, such as an environmental response measurement, back to their respective sources results in a Lagrangian transport plume.

For purposes of this document and the appended claims, the term influence function is defined as the continuous geometric intersection of an object in Eulerian coordinate representation (Eulerian object) or Lagrangian coordinate representation (Lagrangian object) with another Eulerian object or Lagrangian object. For example, the continuous geometric intersection of a Lagrangian transport plume with a Eulerian surface yields one type of surface influence function. The integral over an influence function is unity. Discretizing the continuous influence function to the space resolution of a gridded Eulerian object yields discrete influence weights. For example, discretizing the continuous surface influence function of the Lagrangian transport plume to the space resolution of a gridded Eulerian surface yields one type of discrete surface influence weights. The sum of all influence weights is unity. The influence weights resemble the relative information contribution of each Eulerian grid cell to the information aggregate at their joint destination. For example, the surface influence weights of the Lagrangian transport plume resemble the relative information contribution of each grid cell on the Eulerian surface to the environmental response measurement.

For purposes of this document and the appended claims, the term natural environment is defined as all living and non-living things in a physical region without human influence. A natural environment includes, but is not limited to a planetary geosphere, pedosphere, hydrosphere, biosphere; atmosphere and their astronomical interactions such as sun-earth interaction.

For purposes of this document and the appended claims, the term anthropogenic environment is defined as living and non-living things that exist in a physical region as a result of human influence. The anthropogenic environment can include anthropogenic infrastructure such as infrastructure used for fossil fuel extraction, transportation (including both stationary infrastructure and vehicles), buildings, telecommunications networks, and anything else that is human created or human influenced. Further examples of human interference that characterize the anthropogenic environment include but are not limited to agriculture, forestry, and other alterations of the natural environment because of humans such natural environment feedbacks to human activity. Whenever the term environment is used in this document and/or claims, it can refer to either the natural environment, the anthropogenic environment or a combination of both.

2. Improvement of Measurement Accuracy and Resolution Through Co-Variance

In one embodiment the present invention comprises a method for enhancing environmental data by combining the information content of at least three environmental input sources that at least partially co-vary (i.e., correlate) with each other. The three environmental input sources comprise at least one environmental response and at least two environmental drivers that co-vary with this response. The relationships between these input sources are evaluated to produce a best-fit driver-response model. This best-fit driver response model is combined with the original driver input data to produce environmental response output data that is enhanced in one or more of the following ways relative to the environmental response input data:

(a) The environmental response output data has improved accuracy (i.e., fewer systematic errors);
(b) The environmental response output data has improved precision (i.e., fewer random errors);
(c) The environmental response output data has higher time resolution (i.e., higher frequency);
(d) The environmental response output data has higher space resolution (i.e., higher granularity);
(e) The environmental response output data has higher time coverage (i.e., extends over a broader range of times); and/or
(f) The environmental response data has higher spatial coverage (i.e., extends over a broader range of locations in one, two or three-dimensional space).

3. Detailed Description of One Embodiment

Referring now to the drawings, FIG. 1 shows a processor for combining environmental response input data 0110 and environmental driver input data 0120 for a natural environment into a space and time aligned dataset 0130, that can be used to generate a driver-response process model 0140, to then produce environmental response output data 0150 of improved accuracy, precision, random error, systematic error, and/or resolution, extent and coverage in space and/or time compared to the input environmental response data 0110.

Referring to 0110 in FIG. 1, when trying to collect data in a natural environment, it can be expensive and/or unfeasible to measure certain environmental responses at a sufficient number of locations (i.e. space resolution, space extent and space coverage) and/or with sufficient repetition rate and duration (i.e. time resolution, frequency, time extent and time coverage) to generate a clear representation of the physical phenomena under investigation. Examples of environmental responses that are expensive and/or unfeasible to measure with sufficient resolution, extent and coverage in space and/or time can include:

(a) Momentum flux;
(b) Energy flux, including but not limited to radiative flux and heat flow;
(c) Mass flux of passive scalars including but not limited to the flows of $H_2O$, $CO_2$, $CH_4$, and of reactive scalars including but not limited to the flows of $O_3$, $NO_y$, volatile organic compounds;
(d) Particle flux, including but not limited to the flow of particulate matter in air;
(e) Liquid fluid flux, including but not limited to the flow of a pollutant species in a river;
(f) Other types of fluxes, including but not limited to magnetic flux, electric flux, luminous flux, diffusion flux, volumetric flux, and acoustic flux.

Figure 2A:
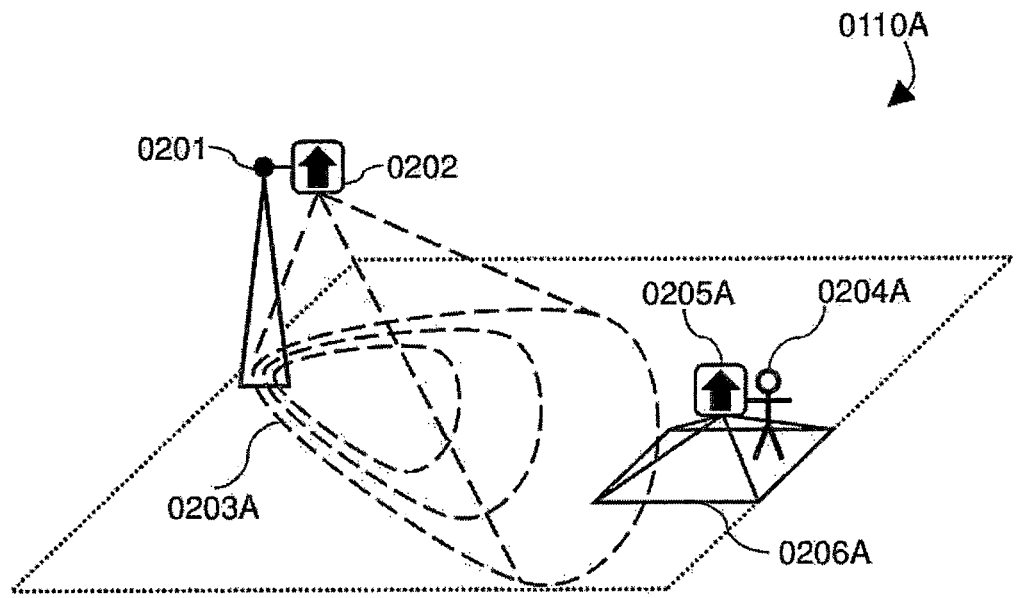
FIG. 2A and FIG. 2B show examples of how environmental response input data is typically generated.
Figure 2B:
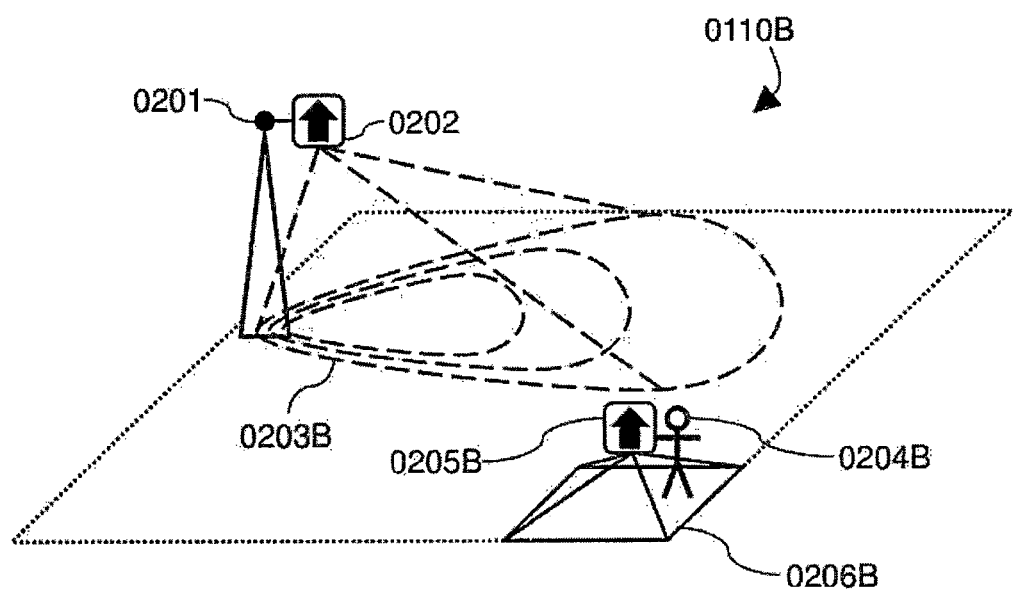

It should be noted that the oblique cone shown at 0203 in FIG. 1, 0203A in FIG. 2A, and 0203B in FIG. 2B is a Lagrangian transport plume that can vary in time as a function of wind direction and other environmental factors. In the Lagrangian coordinate representation fluid parcels are followed through time, from the environmental response under investigation. One example of such a measurement is a surface emission of $H_2O$, which can be followed to a measurement location shown at 0202 in FIG. 1, FIG. 2A, and FIG. 2B atop a support infrastructure shown at 0201 in FIG. 2A and FIG. 2B. The planar (or other shaped) surface under investigation at the base of the Lagrangian transport plume is shown in the symmetric and regular Eulerian coordinate representation, i.e. defined by location and time in a fixed frame. As the result of atmospheric blending occurring in the Lagrangian transport plume, the measured response aggregates over many fluid parcels that originated at a distance from the Eulerian surface under investigation. The aggregate, asymmetric and irregular surface influence function of the measured response can be shown by intersecting the Lagrangian transport plume with the Eulerian surface. The cycloid surface contours shown at 0203 in FIG. 1, 0203A in FIG. 2A, and 0203B in FIG. 2B can be used to represent a given percentile of this surface influence function.

Referring to 0120 in FIG. 1, there are many environmental drivers (factors that cause environmental changes) that can be measured relatively easily, quickly, inexpensively, accurately, precisely, and/or at a high resolution, extent and coverage in space and/or time. Examples of first environmental drivers (0121) and second environmental drivers (0122) that are relatively easy, quick and/or inexpensive to measure at high resolution, extent and coverage in space and/or time can include:

(a) Temperature can be measured in-situ using Ohm's law based on the electrical resistance of metals, and remotely using Planck's law for black body radiation based on the infrared spectrum of emitted electromagnetic light;
(b) Humidity can be measured using Coulomb's law, in-situ based on the dielectric constant of a polymer or metal oxide, and remotely based on the relationship of radar backscatter and an objects dielectric constant;
(c) Solar radiation can be measured using Planck's law for black body radiation in-situ and remotely based on different spectral bands of emitted electromagnetic light;
(d) Other types of environmental drivers can be measured using above and additional physical laws and mathematical models, in-situ and/or remotely, including but not limited to albedo, vegetation indices, land cover, anthropogenic infrastructure, land use (including anthropogenic infrastructure), topography, geologic data, wind, scalar concentration, particle count and size distribution, and other information on the anthropogenic environment and/or the natural environment.

Driver measurements 0120 can relate to the response measurements 0110 through laws of science. Examples of physical laws and mathematical models that can be used to relate driver input data 0120 to response input data 0110 can include:

(a) Conservation of mass;
(b) Conservation of (linear and/or angular) momentum;
(c) Conservation of energy; (d) Navier-Stokes equation;
(e) Reynold's decomposition (turbulent fluid flow analysis);
(f) Fick's laws of diffusion;
(g) Darcy's law of fluid flow;
(h) Newton's law of viscosity;
(i) Fourier's law of conduction;
(j) Flux-gradient similarity;
(k) Profile equations;
(l) Monin-Obukhov similarity;
(m) Bowen-ratio similarity;
(n) Flux-variance similarity;
(o) Transport models;
(p) Advection, diffusion and dispersion models;
(q) Resistance models;
(r) Evapotranspiration models;
(s) Reactive decay models; (t) Closure techniques.

Provided that the surface influence functions of response input data 0110 and driver input data 0120 overlap at least fractionally in space and time, they can be measured with the same or different instruments deployed at the same or different locations. Here, the response measurement at 0202 in FIG. 1, FIG. 2A, and FIG. 2B is shown in Lagrangian coordinate representation, i.e. fluid parcels are followed through time, and the driver measurements 0120 are shown in Eulerian coordinate representation, i.e. defined by location and time in a fixed frame. Eulerian-to-Lagrangian convolution can be used to generate a space-aggregated perspective, and Lagrangian-to-Eulerian de-convolution can be used to generate a space-resolved perspective. Note that environmental responses can also be depicted in the Eulerian representation such as at 0205A in FIG. 2A and at 0205B FIG. 2B, and environmental drivers can also be depicted in the Lagrangian representation.

Further referring to FIG. 1, the response measurements 0110, first driver measurement 0121 and second driver measurement 0122 can be aligned from their respective source coordinate representations into a shared intermediary coordinate representation using steps 0131 and 0132 shown in box 0130. In the embodiment shown in FIG. 1, the space and time aligned data table 1141 therein is achieved through convolving the first driver measurement 0121 and second driver measurement 0122 from their Eulerian source coordinate representation to the Lagrangian coordinate representation of the response measurements. This is accomplished by combining the driver measurements 0120 at target space and time resolutions with the surface influence functions of the response measurements 0110, resulting in the space-time-aligned, co-interpretable training dataset 1141. This alignment is performed in step 0131, which is explained in detail in FIG. 4 (steps 0414 to 0431) and in step 0132, which is explained in detail in FIG. 11 (steps 1110 to 1140). The space-time extent of the training dataset 1141 comprises the fractional overlap in space and time among the intersected responses and drivers. Because the environmental response measurements 0110 are comparatively sparse, they also limit the joint space-time extent.

Figure 12:
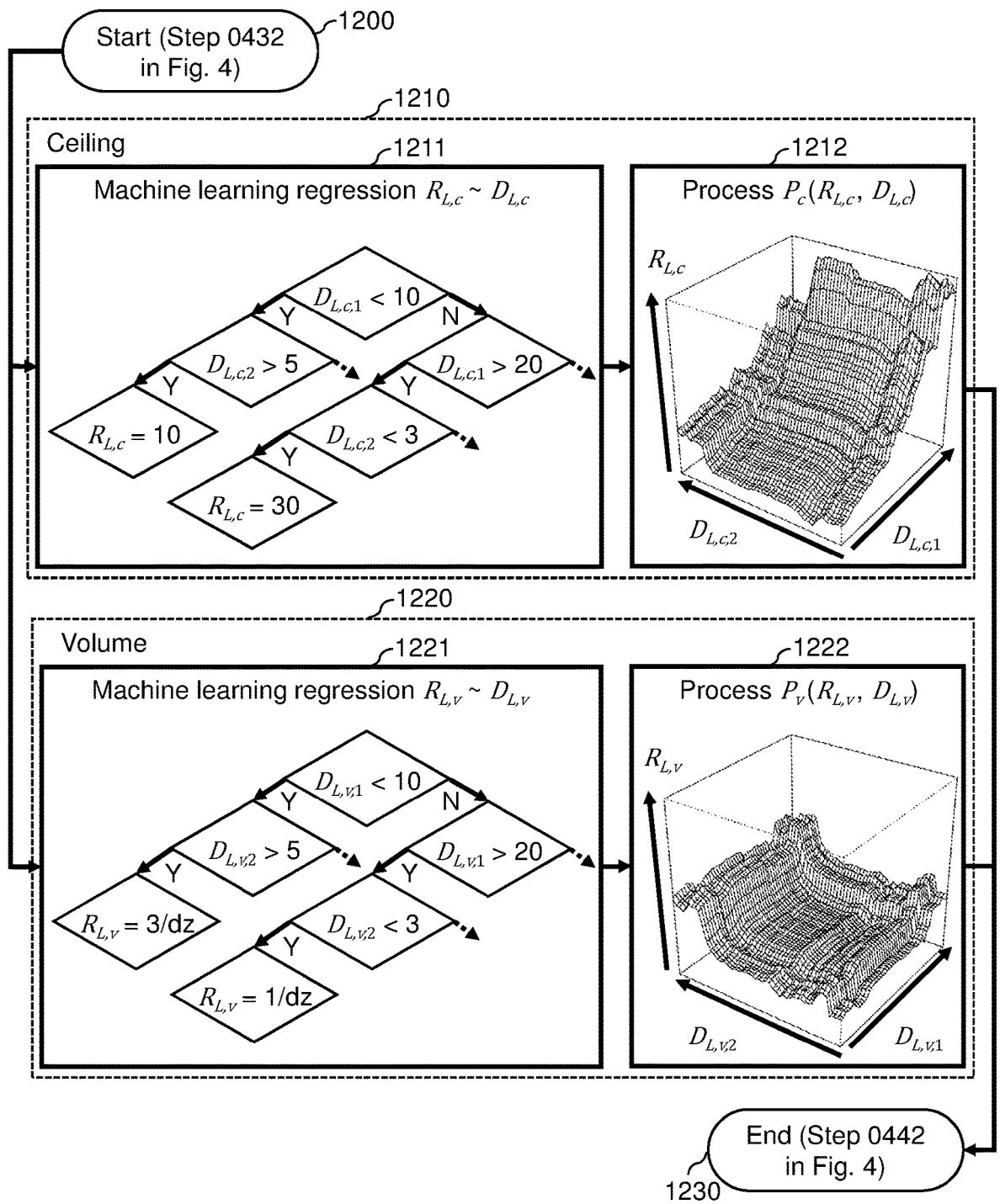
FIG. 12 shows how the driver-response relationship model is created.

Continuing with the method illustrated in FIG. 1, machine learning and other techniques capable of being understood by those skilled in the art (such as least squares multivariate regression) can be used to generate a driver-response process model 0140 from the space and time aligned dataset. The structure of the process model 0140 results from the responses and drivers chosen to represent a law of science. For example, if the environmental response input data 0110 are $H_2O$ flux responses, they can be related through Fick's first law of diffusion to a humidity gradient driver. In this specific example, machine learning (and other techniques) can be used to determine the $H_2O$ turbulent diffusion coefficient as a multi-variate and co-dependent function of the humidity gradient driver (measured at 0120), alongside temperature and solar radiation drivers (also measured at 0120). The result is a driver-response process model across the range of intersected responses and drivers in the space and time aligned dataset 1141 used for machine learning. FIG. 12 provides additional detail. Among others, the generated driver-response process model can be used directly to benchmark other, existing process models.

Finally, in 0150, the system produces the space-time resolved environmental responses 1330 by applying the generated driver-response process model 0140 to the jointly space-time resolved environmental driver measurements 0120. In 0151 the expensive information contained in the sparse environmental response measurements 0110 is thus projected across the target coordinate representation, space and time extent and resolution, and abundance of the environmental driver measurements 0120, which is explained in more detail in FIG. 13. This reduces the cost per unit space and time for obtaining environmental responses compared to their measurement 0110 alone. In the current example, the resulting Eulerian fixed-frame coordinate representation 1330 improves interoperability with other environmental measurements and models, and reduces uncertainty through explicitly addressing all terms in the conservation equation underlying the $H_2O$ flux response measurements 0110.

Referring generally to the method illustrated in FIG. 1, it should be noted that environmental drivers, such as those illustrated and described with reference to 0120, and environmental responses, such as those illustrated and described with reference to 0110, do not necessarily need to come directly from measurement instruments. Such environmental drivers 0120 and environmental responses 0110 can also be outputs of mathematical process models, e.g., the re-analysis of data that was collected in other ways to optimize future instrument field deployments. The outputs of the foregoing steps 0140 and 0150 can be used for control as shown at 0160 and described later in this document.

FIG. 2A and FIG. 2B show examples of how environmental response input data is-typically generated. In-situ environmental response measurements such as shown at 0202, 0205A and 0205B capture a wide range of physical phenomena, but are often expensive and/or unfeasible to measure with sufficient resolution, extent and coverage in space and/or time. For measurements from towers as shown at 0201 the environmental hardening required for automated deployment and operational expenses can be cost-prohibitive. The same constraint applies to deployment of such measurement instruments in other ways than towers, such as ships, buoys, aircraft, etc. Examples of typical instruments used for such automated deployments include a 3-dimensional sonic anemometers (e.g., CSAT-3; Campbell Scientific, Inc.; Logan, Utah) in combination with a $CO_2/H_2O$ infrared gas analyzer (e.g., LI-7200; LICOR, Inc.; Lincoln, Nebraska). Similarly, the manual labor cost for human observers as shown at 0204A, 0204B can be cost-prohibitive. Examples for typical instruments used by human observers include a portable $CO_2/H_2O$ infrared gas analyzer (e.g., LI-870; LI-COR, Inc.; Lincoln, Nebraska), and a portable optical gas imaging camera (e.g., GF620; FLIR Systems, Inc.; Wilsonville, Oregon). Also, the number of deployments necessitated by the limited and varying resolution, extent and coverage in space and/or time of each measurement as shown at 0203A, 0203B, 0206A and 0206B can be cost-prohibitive. Specifically, the influence function of the tower-mounted in-situ measurements shown at 0203A can aggregate in space over irregular, changing surface areas as a function of wind direction and other environmental factors, shown at 0203B. Similarly, the influence function of the human observer in-situ measurement shown at 0206A can aggregate in space over surface areas that are smaller in comparison to the automated tower measurements, and change as a function of observer location shown at 0206B. It is important to note that certain types of environmental responses become accessible also by proximal- and remote-sensing technologies, such as 3-dimensional wind Doppler light detection and ranging (e.g., StreamLine XR; Halo Photonics; Worcester, United Kingdom), and water vapor and temperature Raman light detection and ranging (e.g., SRLID; Atmospheric Radiation Measurement; Richland, Washington). The minimum requirement for environmental response input data is that they are sufficiently resolved to generate a clear representation of the physical phenomena under investigation either in space or in time.

Figure 3A:
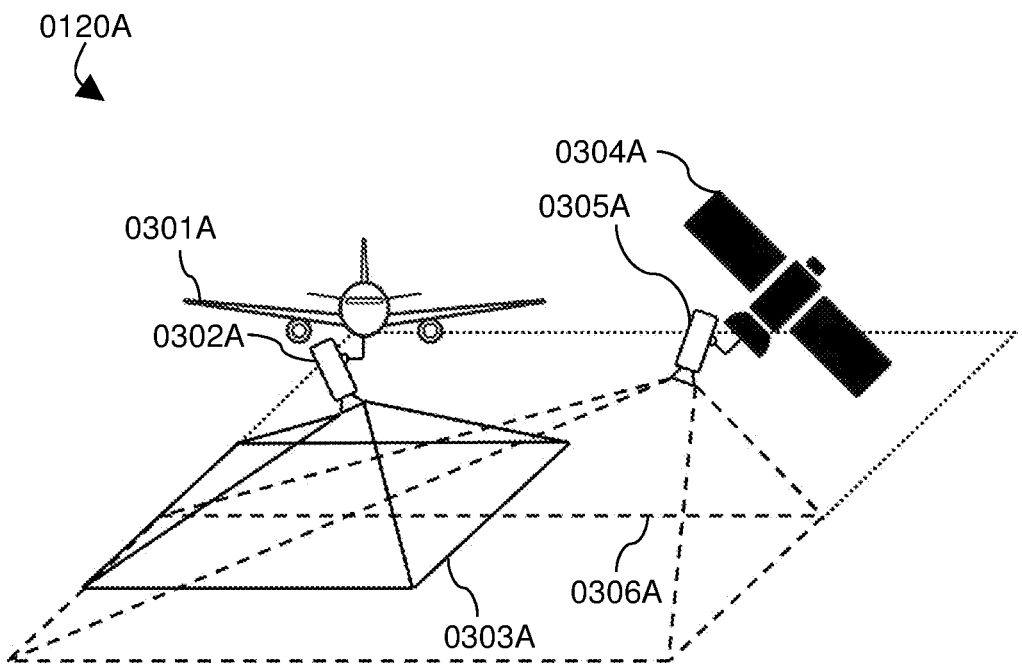
FIG. 3A and FIG. 3B show examples of how environmental driver input data is typically generated.
Figure 3B:
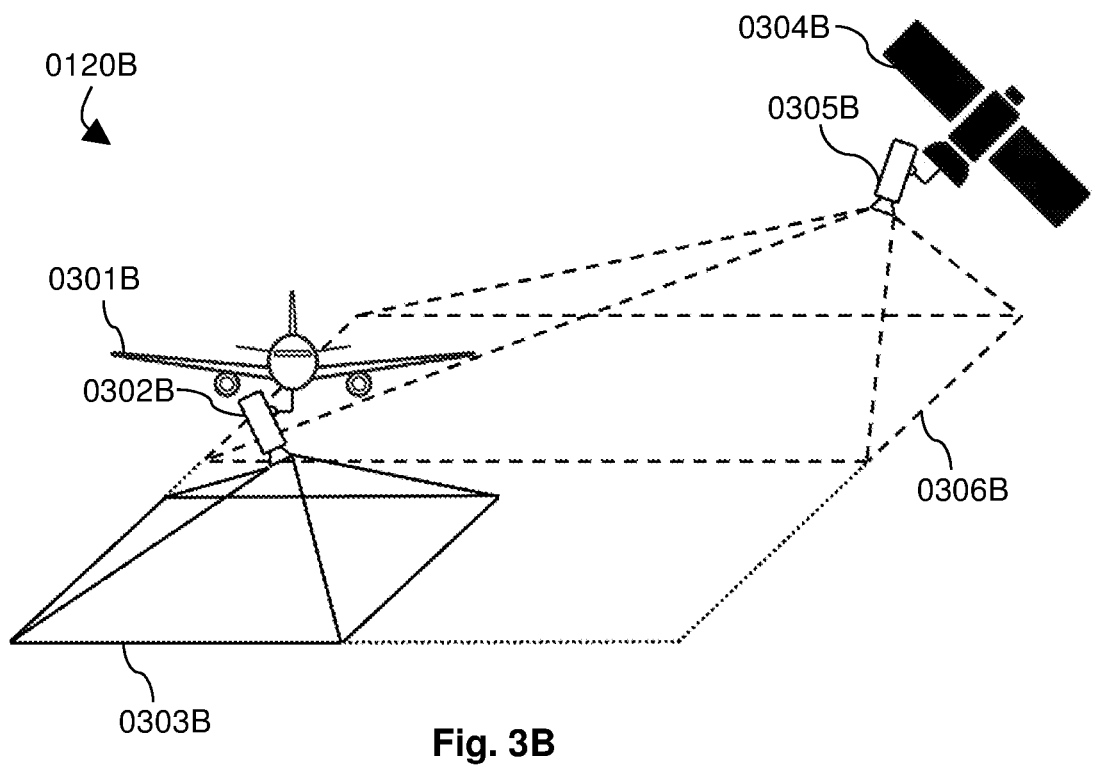

FIG. 3A and FIG. 3B show examples of how environmental driver input data is typically generated. Remote sensing environmental driver measurements from aircraft such as shown at 0301A, 0301B and from satellite such as shown at 0304A and 0304B capture only a subset of physical phenomena compared to the environmental response measurements, but are often comparatively easy, quick and inexpensive to measure at high resolution, extent and coverage in space and/or time. Examples for typical instruments used for remote sensing environmental driver measurements such as shown at 0302A, 0302B, 0305A and 0305B include a discrete return Doppler light detection and ranging (e.g., ALTM Gemini; Optech, Inc.; Vaughan, Ontario, Canada) and an imaging spectrometer (e.g., AVIRIS-NG; California Institute of Technology; Pasadena, California). The regular influence function of the aircraft and satellite operated remote sensing measurements shown at 0303A and 0306A results solely from line-of-sight geolocation and thus resolves individual surface areas in space. This influence function can change as a function of aircraft and satellite location shown at 0303B and 0306B. The minimum requirement for environmental driver input data is that at least one driver is sufficiently resolved in space, and at least one driver is sufficiently resolved in time, to jointly generate a clear representation of the physical phenomena under investigation in space and time.

Figure 4:
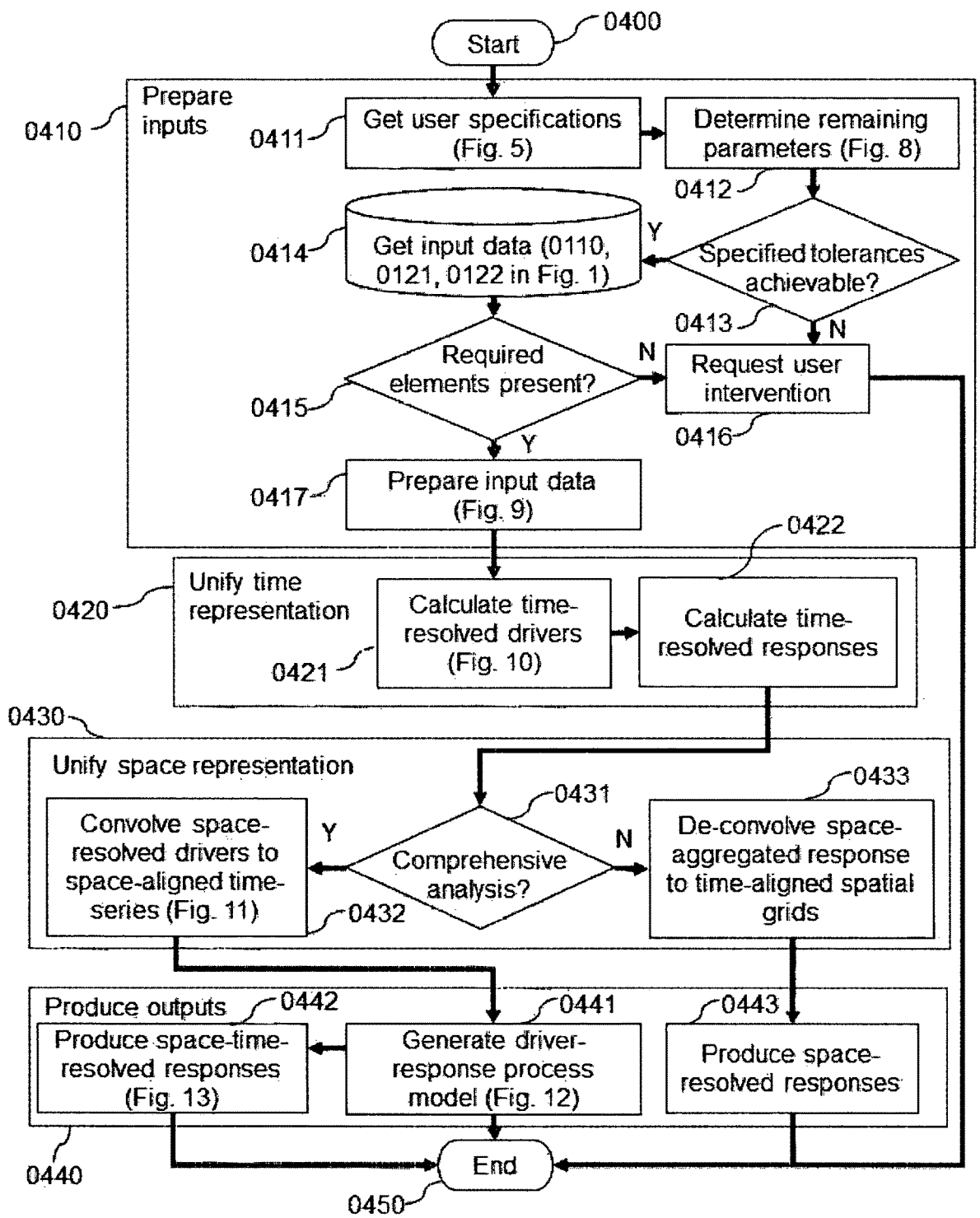
FIG. 4 shows a set of steps for processing the data needed to implement the method of FIG. 1.

FIG. 4 illustrates an overall process for complementing space-aggregated/time-resolved, sparse and expensive environmental response measurements 0110 with jointly space-time resolved, abundant and inexpensive environmental driver measurements 0120. The process shown in FIG. 4 encompasses the items shown as modules at 0130, 0140 and 0150 in FIG. 1. The process itself consists of four main functional blocks to prepare inputs 0410, unify time representation 0420, unify space representation 0430, and produce outputs 0440. The combination of the prepare inputs 0410, unify time representation 0420, and unify space representation 0430 functional blocks produce the space and time aligned dataset 1141, shown in FIG. 1.

Figure 5:
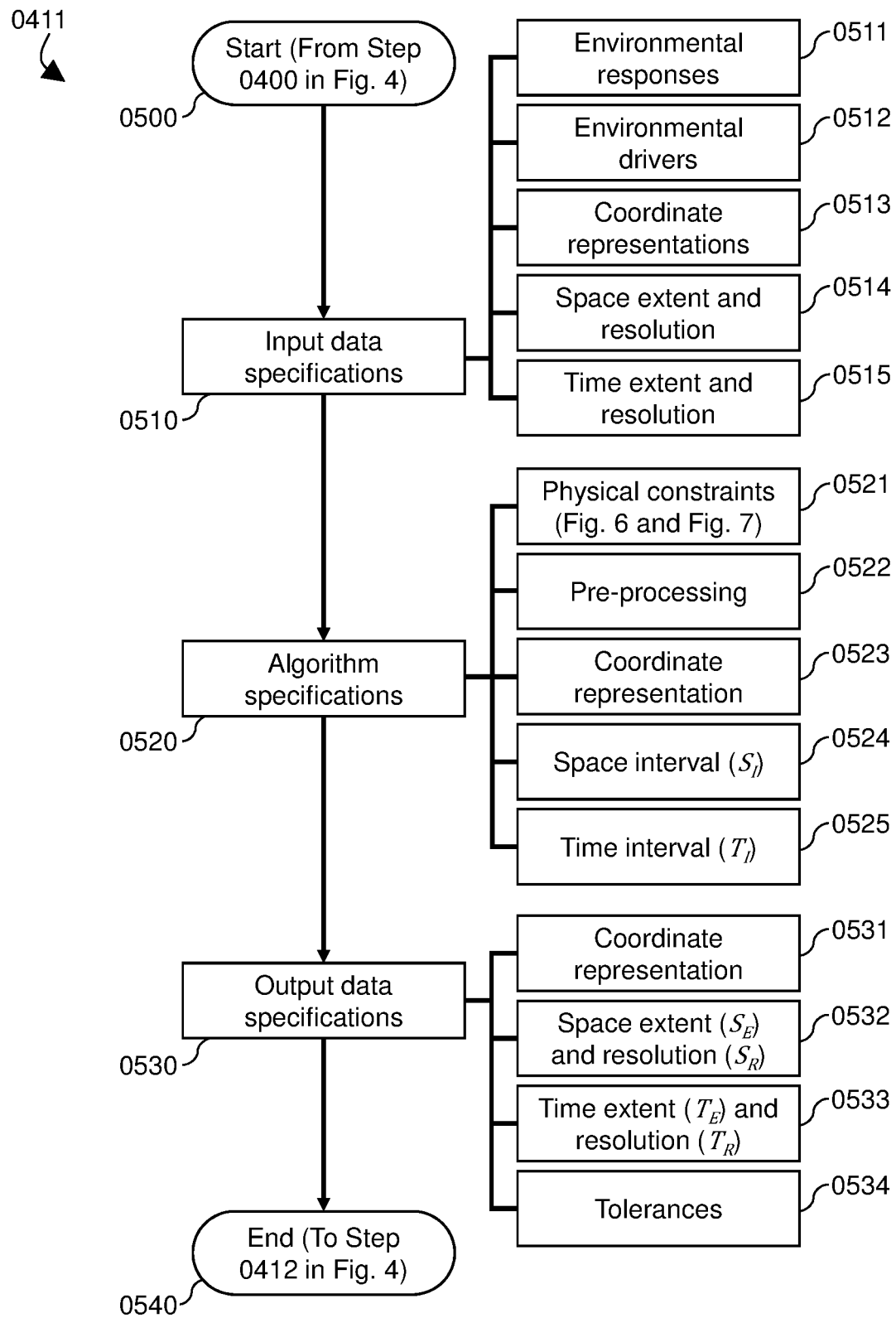
FIG. 5 details Step 0411 (Get user specifications) of FIG. 4.
Figure 8:
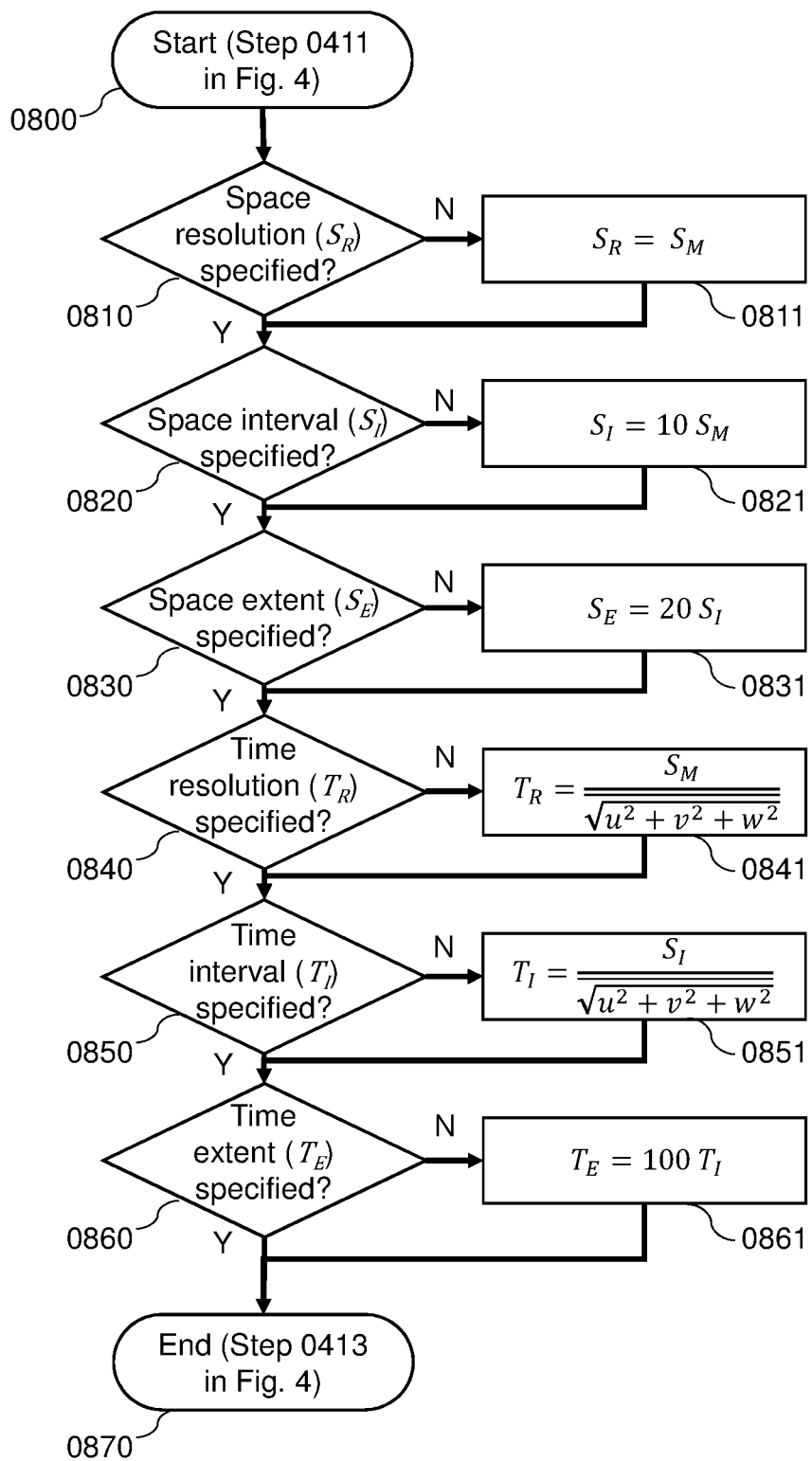
FIG. 8 shows the default settings of parameters for the execution one embodiment of the inventions described herein.

Referring to module 0410 in FIG. 4, the process to prepare inputs commences with getting user specifications 0411, as further detailed in FIG. 5, and determining remaining parameters 0412, as further detailed in FIG. 8. Next, the process tests the tolerances 0413 specified as part of the user specifications 0411. If the tolerances are achievable, the process obtains input data 0414, or requests user intervention otherwise 0416. Next, the process tests whether all required elements are present 0415 in the user specifications 0411, remaining parameters 0412 and input data 0414, which are shown as response input data 0110, first driver input data 0121, and second driver input data 0122 in FIG. 1. If all required elements are present, the process prepares the input data 0417, as further detailed in FIG. 9, or requests user intervention otherwise 0416.

Referring to module 0420 in FIG. 4, the process to unify time representation first obtains all univariate time-series from the prepared input data 0417 above. A time-domain box filter can be used to calculate the space-aggregated/time-resolved drivers 0421, as further detailed in FIG. 10, such as air temperature and humidity at the time resolution $T_R$ for each time interval $T_1$ over the time extent $T_E$, alongside wind direction for use in the unify space representation module 0430 below. Expanding the use of the box filter to the time-frequency domain yields the space-aggregated/time-resolved responses 0422, such as the $H_2O$ flux for the same $T_R$, $T_1$ and $T_E$ as the meteorological states above. First the base states for all univariate time-series are calculated and subtracted over $T_E$. In step 0411 above the user can chose between arithmetic mean, linear trend and polynomial base states. Next, the process uses time-frequency decomposition such as Wavelets to decompose the univariate time-series into time-frequency signal pairs at the time resolution native to the environmental response measurements 0110. From these the time-frequency-resolved variances (here: Wavelet scalograms) and co-variances (here: Wavelet cross-scalograms) are calculated, and corrected with a transfer function for high-frequency spectral loss. Next, the process integrates the corrected time-frequency-resolved variances and co-variances across the frequency-domain, which yields variance and co-variance timeseries still at the time resolution native to the environmental response measurement 0110. Finally, the same time-domain box filter as in step 0421 is used to yield the space-aggregated/time-resolved environmental responses such as $H_2O$ flux for the same $T_R$, $T_1$ and $T_E$ as the space-aggregated/time-resolved environmental drivers 0421 above, alongside turbulence statistics for use in the unify space representation module 0430 below.

Figure 10:
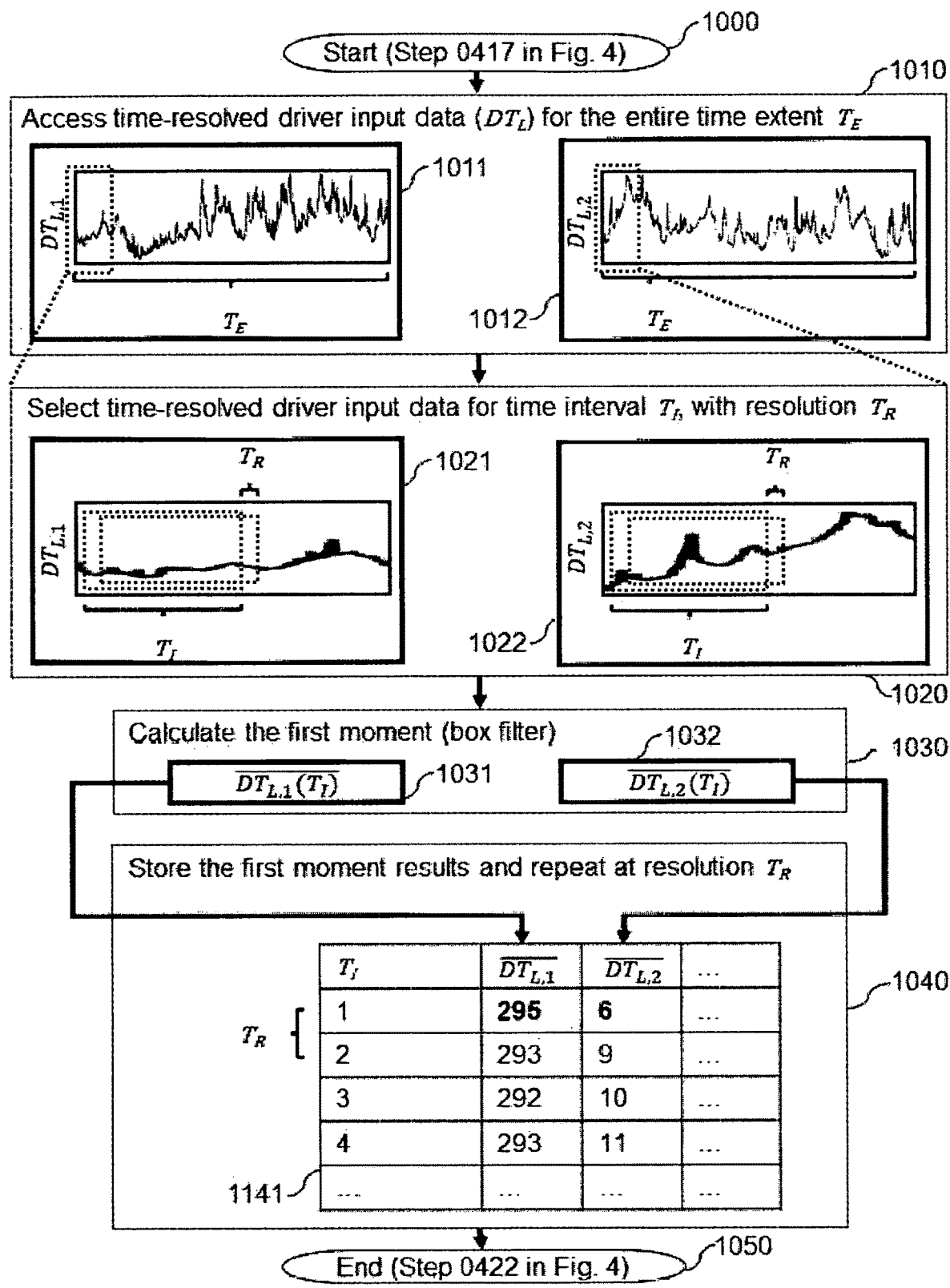
FIG. 10 shows how a space and time aligned data table can be initiated by creating a reference time representation and processing the time-resolved drivers.

Referring to the unify space representation module 0430 in FIG. 4, the process first obtains the space-resolved/time-aggregated environmental drivers from step 0414, also shown at 0121 in FIG. 1, the space-aggregated/time-resolved environmental drivers from step 0421, also shown at 1040 in FIG. 10, and the space-aggregated/time-resolved environmental responses from step 0422, also shown at 0130 in FIG. 1. The analysis scope lookup 0431 then queries the user specifications 0411. If comprehensive analysis is selected, the process creates a space-aligned time-series via convolving the space-resolved/time-aggregated environmental drivers to the coordinate representation of the space-aggregated/time-resolved responses 0432, as further detailed in FIG. 11, here Lagrangian for the $H_2O$ flux. If comprehensive analysis is not selected, the process creates time-aligned spatial grids via de-convolving the space-aggregated/time-resolved responses, here the $H_2O$ flux, to the coordinate representation of the space-resolved/time-aggregated environmental drivers 0433, here Eulerian. If flux data is selected as environmental driver input, this flux type is different from the type of flux corresponding to the environmental response input flux data. If both of the environmental driver input data are fluxes, they need to be different from each other as well as from the response.

Referring to the produce outputs module 0440 in FIG. 4, if the analysis scope lookup 0431 directs to the comprehensive analysis, the process first obtains the space-aligned time-series from step 0432. This space-aligned time series was also shown at 1141 in FIG. 1. Machine learning (or other techniques capable of being understood by anyone skilled in the art) can then be used to generate the multivariate and co-dependent driver-response process model 0441, which was illustrated at 0140 in FIG. 1 and will be explained in greater detail in FIG. 12, across the range of assimilated environmental responses and drivers in the space-aligned time-series 0432 (that was also shown at 1141 in FIG. 1). The process then produces the space-time resolved environmental responses 0442 (that were also illustrated at 1330 in FIG. 1) by applying the generated driver-response process model 0441 to the space-resolved/time-aggregated environmental drivers from step 0414 and the time-resolved/space-aggregated environmental drivers from step 0421. This process of generating the time and space resolved responses 0442 (which is also called the environmental response output data 1330 in FIG. 1) will be further explained in FIG. 13. If the analysis scope lookup 0431 does not direct to the comprehensive analysis, the process obtains the time-aligned spatial grids 0433, and formats them according the user specifications 0411 to produce quick-looks 0443.

FIG. 5 illustrates an overall process for getting user specifications, which encompasses the items shown at 0400, 0411 and 0412 in FIG. 4. The process itself consists of the three main functional blocks to obtain input data specifications 0510, algorithm specifications 0520, and output data specifications 0530.

Referring to step 0510 in FIG. 5, the process to obtain input data specifications includes but is not limited to defining environmental responses 0511, environmental drivers 0512, their respective coordinate representations 0513, as well as their respective resolutions and extents in space 0514 and time 0515.

Referring to step 0520 in FIG. 5, the process to obtain algorithm specifications commences with defining physical constraints 0521 based on laws of science and existing mathematical models, for which a detailed example is given in FIG. 6. Additional algorithm specifications include but are not limited to parameters for pre-processing 0522, including parameters for range test, persistence test, step test, spike test, acceptable data fraction, streamline rotation, regularization, time synchronization, and definition of synthetic variables, as detailed in FIG. 9. Next, the coordinate representation 0523 including type of analysis for creating the space and time aligned data set 1141 and 0430 are defined. Lastly, space interval 0524 and time interval 0525 for algorithmic processing are specified.

Referring to step 0530 in FIG. 5, the process to obtain output data specifications includes but is not limited to defining the output coordinate representation 0531, space extent and resolution 0532, time extent and resolution 0533, as well as output data tolerances 0534.

FIG. 6 illustrates how space-time de-convolution and subsequent ensembling reduce the $H_2O$ flux conservation equation to two differential equation terms that are fully quantifiable through the systems and methods described in this invention, thus order-of-magnitude improving tolerances compared to existing approaches. The method shown in FIG. 6 applies to the items shown as module at 0150 in FIG. 1, and steps 0441 and 0442 in FIG. 4. The method itself consists of three main modules, the full $H_2O$ flux conservation equation for a single unit cube 0610, canceling horizontal transport terms in an ensemble of unit cubes 0620, and canceling horizontal-compensatory fluxes in an ensemble of unit cubes 0630, resulting in the reduced $H_2O$ flux conservation equation for an ensemble of unit cubes. The method commences with the full $H_2O$ flux conservation equation for a single unit cube 0610.

Space ensembling the horizontal transport terms over many unit cubes then effectively cancels them from the $H_2O$ flux conservation equation 0620. This is achieved through constructing a square grid of N×N unit cubes with a single vertical layer 0621. With increasing N the relative contribution of $H_2O$ transport through the along-wind and cross-wind walls to the $H_2O$ flux conservation equation trends towards zero 0622. Considering all terms in the $H_2O$ flux conservation equation for a unit cube 0610 being of similar magnitude, the tolerance in cancelling the horizontal transport terms 0623 is proportional to the fractional area they represent in the N×N ensemble.

The full $H_2O$ flux conservation equation for a single unit cube 0610 further shows that any non-zero horizontal transport results in corresponding changes in the remaining two differential equation terms. Such horizontal-compensatory fluxes however do not originate from within the unit cube, and would thus falsify estimation of the net $H_2O$ flux after dropping the horizontal transport terms 0622. Space ensembling the remaining terms $H_2O$ accumulation in volume and $H_2O$ transport through ceiling over many unit cubes 0631 also effectively cancels these horizontal-compensatory fluxes 0630, as exemplified here for the environmental response output data 1330, also shown in FIG. 1 and FIG. 13. This yields the reduced $H_2O$ flux conservation equation for an ensemble of unit cubes 0632, which terms are fully quantifiable through the systems and methods described in this invention, thus order-of-magnitude improving tolerances compared to existing approaches. The tolerance in canceling the horizontal-compensatory fluxes 0633 is proportional to the standard error of their ensemble mean trending towards zero, as a function of number of unit cubes in the ensemble $N^2$.

Figure 7:
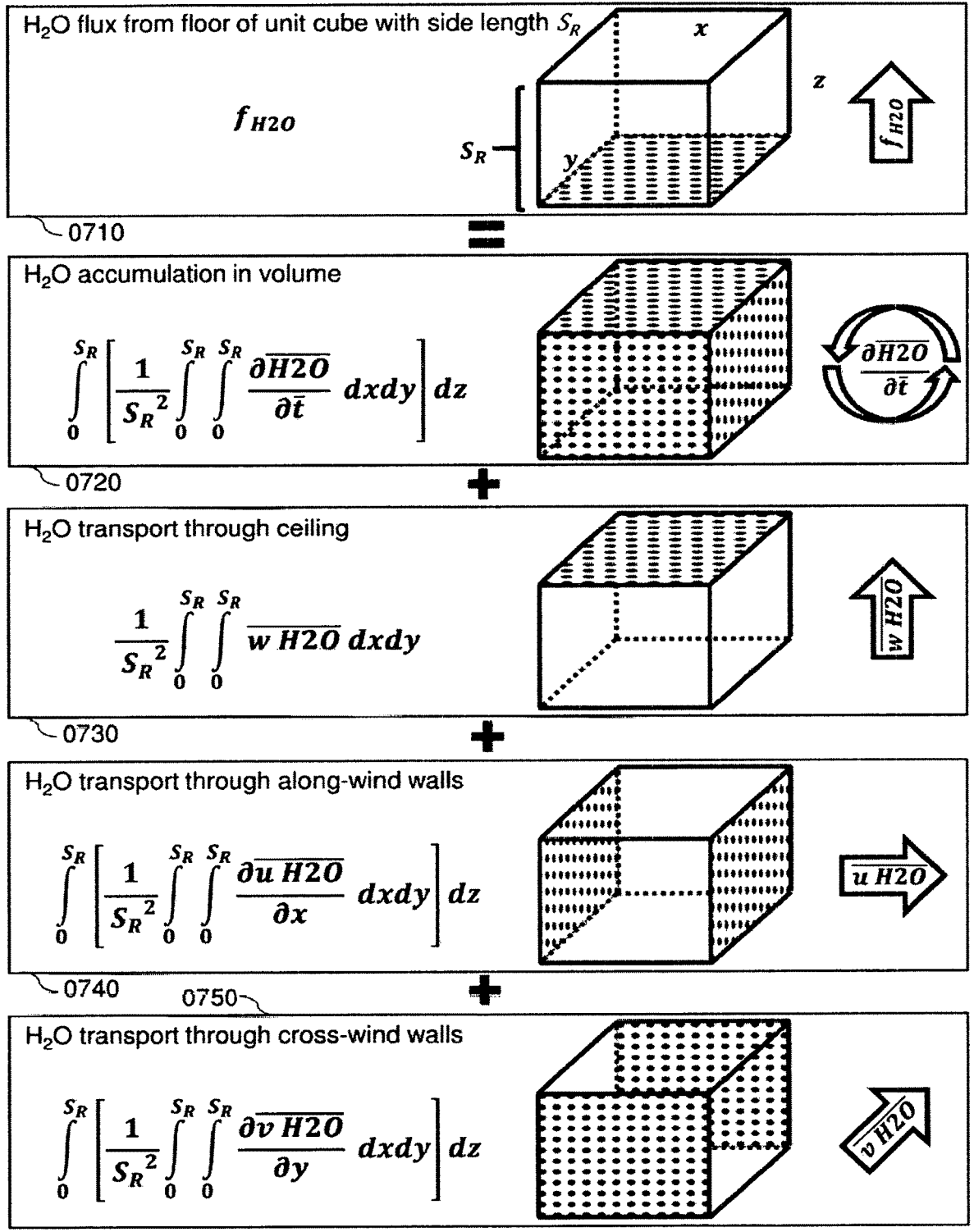
FIG. 7 shows how a physical constraint is constructed based on a law of science, using an $H_2O$ flux conservation equation as an example.

FIG. 7 illustrates how a physical constraint is constructed based on a law of science, encompassing the item shown at 0610 in FIG. 6. Specifically, in this example a constraint on the flux of $H_2O$ from the floor of a unit cube 0710 is constructed from the law of conservation of mass. In this $H_2O$ flux conservation equation the flux of $H_2O$ from the floor of a unit cube 0710 can be expressed as the sum of $H_2O$ accumulation in the unit cube volume 0720, $H_2O$ transport through the unit cube ceiling 0730, $H_2O$ transport through the unit cube along-wind walls 0740, and $H_2O$ transport through the unit cube cross-wind walls 0750.

FIG. 8 illustrates the default settings of parameters required for the execution of the systems and methods described in this invention, if they are not already present in the user specifications 0411. The method shown in FIG. 8 applies to the items shown as steps 0411, 0412 and 0413 in FIG. 4. The method commences with obtaining the user specifications 0800 from step 0411 in FIG. 4. The output space resolution lookup 0810 then queries the user specifications 0800. If the output space resolution is not already present in the user specifications 0800, the method assigns the height above ground of the $H_2O$ transport through ceiling measurement ($S_M$) as default output space resolution 0811. Next, the output space interval lookup 0820 queries the user specifications 0800. If the output space interval is not already present in the user specifications 0800, the method calculates and assigns a default output space interval 0821. Next, the output space extent lookup 0830 queries the user specifications 0800. If the output space extent is not already present in the user specifications 0800, the method calculates and assigns a default output space extent 0831. Next, the output time resolution lookup 0840 queries the user specifications 0800. If the output time resolution is not already present in the user specifications 0800, the method calculates and assigns a default output time resolution 0841 as function of the along—(u), cross—(v) and vertical—(w) wind components. Next, the output time interval lookup 0850 queries the user specifications 0800. If the output time interval is not already present in the user specifications 0800, the method calculates and assigns a default output time interval 0851. Next, the output time extent lookup 0860 queries the user specifications 0800. If the output time extent is not already present in the user specifications 0800, the method calculates and assigns a default output time extent 0861. The method completes with providing the user specifications 0800 alongside any calculated and assigned default parameters to the specified tolerances achievable lookup 0870.

Figure 9:
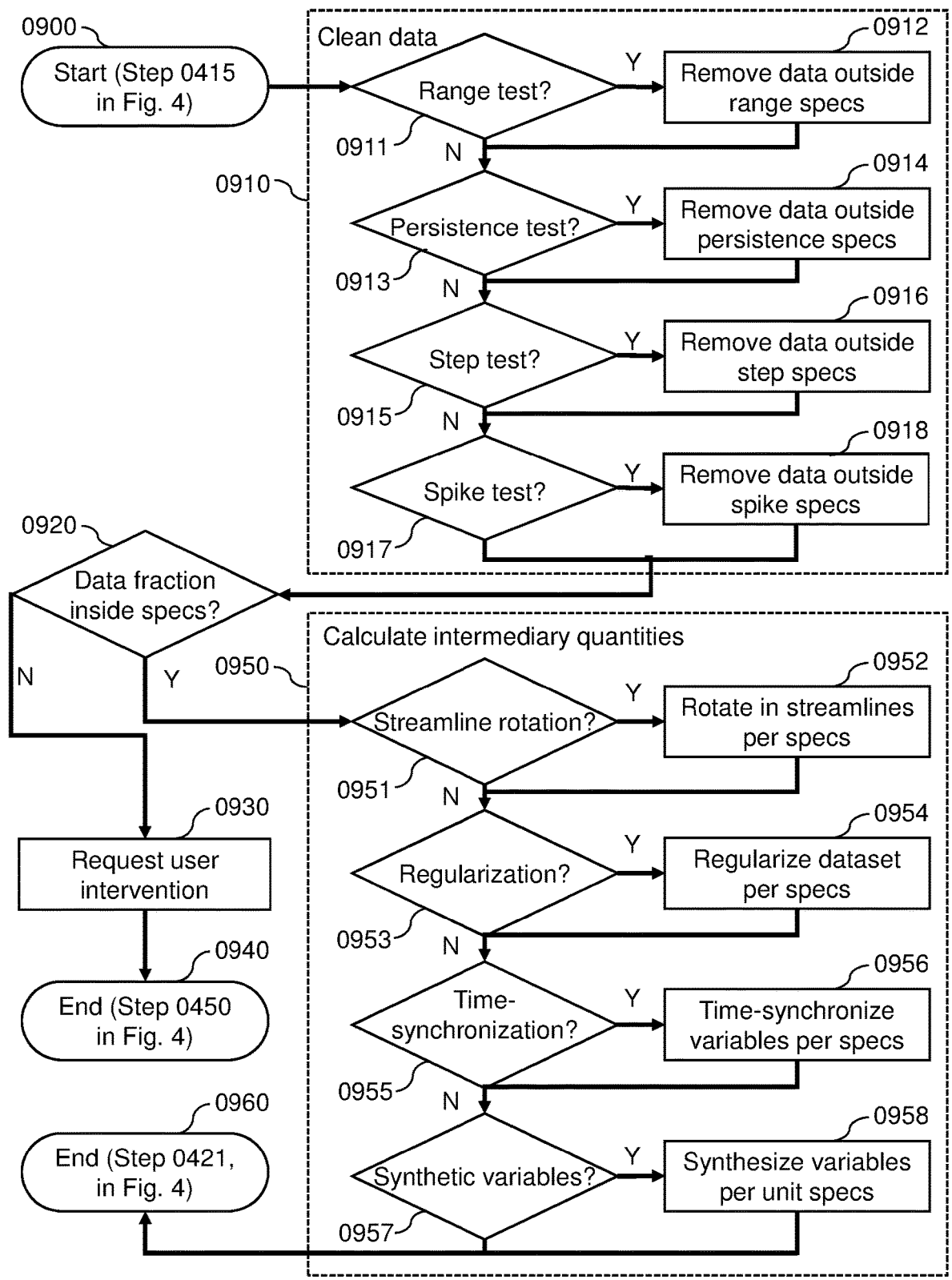
FIG. 9 shows the input data preparation for the execution of the systems and methods described in this invention

FIG. 9 illustrates the input data preparation for the execution of the systems and methods described in this invention. The method shown in FIG. 9 applies to the items shown as steps 0415, 0417 and 0421 in FIG. 4. The method itself consists of two main modules, to clean the input data 0910, and to calculate intermediary quantities 0950.

Further referring to FIG. 9, in module 0910 the range test lookup 0911 first queries the user specifications 0900 from step 0411 in FIG. 4. If the range test is selected, data outside the user specifications are removed at 0912, or no data is removed otherwise. Next, the persistence test lookup 0913 queries the user specifications 0900. If the persistence test is selected, data outside the user specifications are removed at 0914, or no data is removed otherwise. Next, the step test lookup 0917 queries the user specifications 0900. If the step test is selected, data outside the user specifications are removed at 0916, or no data is removed otherwise. Next, the spike test lookup 0915 queries the user specifications 0900. If the spike test is selected, data outside the user specifications are removed at 0918, or no data is removed otherwise. This completes the input data cleaning module 0910.

Further referring to FIG. 9, the data fraction lookup 0920 queries the user specifications 0900. If the remaining data fraction after the input data cleaning module 0910 is outside the data fraction user specifications, user intervention is requested at 0930 and the method ends at 0940. If however, the remaining data fraction is within the user specifications, the method continuous with the intermediary quantity calculation module 0950.

Further referring to FIG. 9, in module 0950 the streamline rotation lookup 0951 first queries the user specifications 0900. If streamline rotation is selected, data are rotated at 0952 according to the user specifications, or no rotation is performed otherwise. Next, the regularization lookup 0953 queries the user specifications 0900. If regularization is selected, data are regularized at 0954 according to the user specifications, or no regularization is performed otherwise. Next, the time synchronization lookup 0955 queries the user specifications 0900. If time synchronization is selected, data are time-synchronized at 0956 according to the user specifications, or no time synchronization is performed otherwise. Next, the synthetic variables lookup 0957 queries the user specifications 0900. If synthetic variables are selected, at 0958 the synthetic variables are computed, or no synthetic variables are computed otherwise. This completes module 0950, and at 0960 the intermediary quantities are reported back to step 0421 in FIG. 4.

FIG. 10 illustrates how the space and time aligned data table 1141 (also shown in FIG. 1) is initiated through creating a reference time representation and processing the time-resolved drivers accordingly. The method shown in FIG. 10 applies to the items shown as steps 0417, 0421 and 0422 in FIG. 4. The method itself consists of four main modules, to access the time-resolved driver input data 1010, to select the time-resolved driver input data for a specified time interval 1020, to calculate the first moment 1030, and to initiate the space and time aligned data table and store the first moment results 1040.

Further referring to FIG. 10, in module 1010 the method commences with accessing the time-resolved driver input data ($DT_L$) for the entire time extent $T_E$, here exemplified for two time-resolved drivers $DT_{L,1}$ shown at 1011 and $DT_{L,2}$ shown at 1012, such as air temperature and humidity. Additional examples for time-resolved driver input data include but are not limited to solar radiation, and wind direction is prepared for later use in the unify space representation module 0430.

Further referring to FIG. 10, in module 1020 the time interval $T_1$ is then selected from the time-resolved driver input data, and subsequently moves through the time extent $T_E$ with the time resolution $T_R$ as shown at 1021 and 1022.

Further referring to FIG. 10, in module 1030 the first moment is then calculated for each time-resolved driver and time interval $T_1$, resembling a box filter and indicated with single overbars over the processed drivers shown at 1031 and 1032.

Further referring to FIG. 10, in module 1040 the first moment results are stored which initiates the space and time aligned data table 1141 (also shown in FIG. 1), and the method is repeated at time resolution $T_R$ over the time extent $T_E$. The above example illustrates the case for time-resolved driver input data that has a higher time resolution compared to the space and time aligned data table, hence using a box filter aggregation approach. Analogously, time interpolation approaches can be used if the time-resolved driver input data that has a lower time resolution compared to the space and time aligned data table. Furthermore, the method is exemplified above for time-resolved driver input data that are collocated with the response input data. Analogously, if the driver input data is time-resolved and space-resolved such as frequently the case for outputs from mathematical process models, the above method applies to each time-resolved grid cell in FIG. 11.

Figure 11:
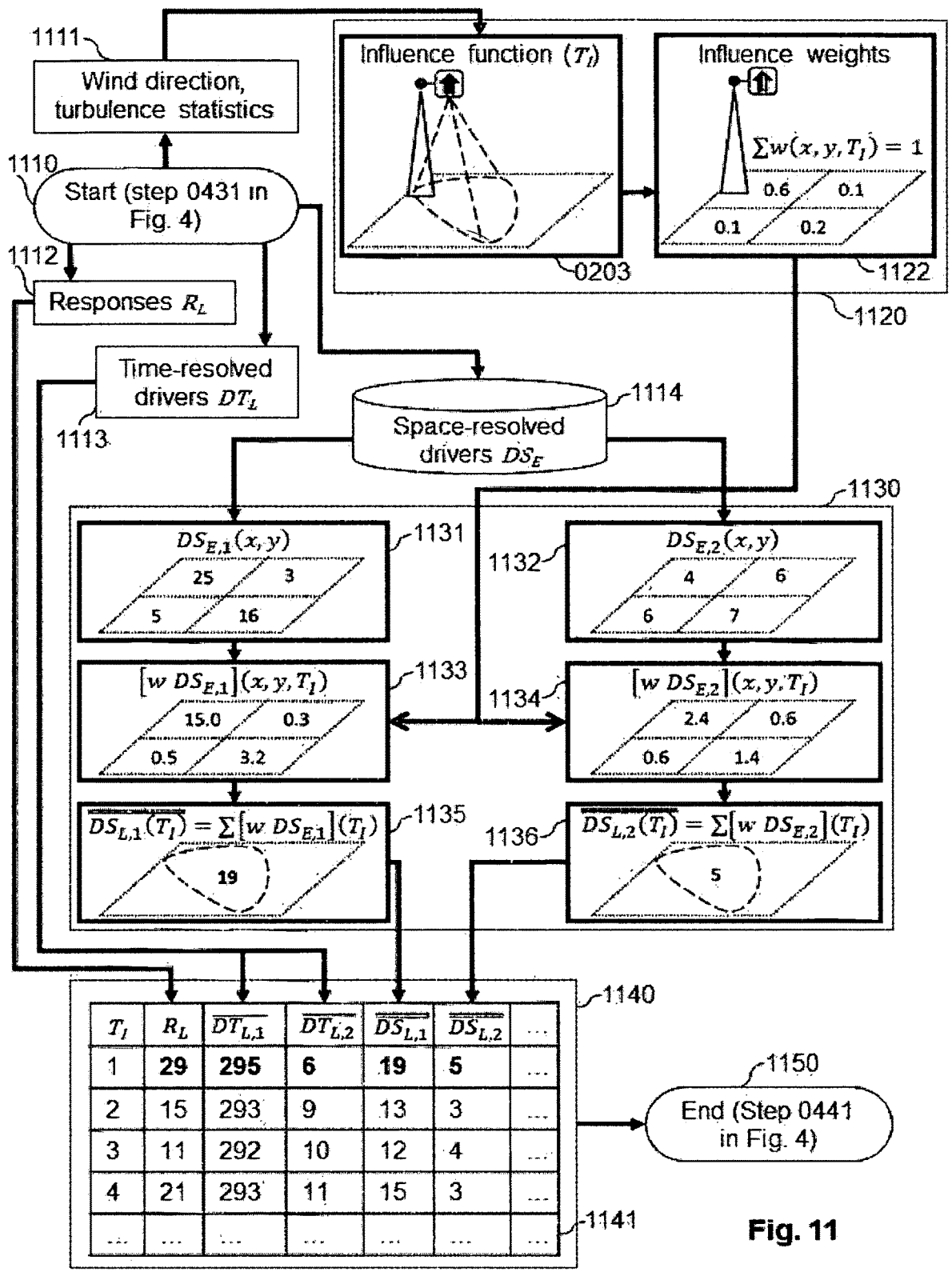
FIG. 11 shows how the space and time aligned data table can be completed by defining an intermediary coordinate representation and processing the space-resolved drivers.

FIG. 11 illustrates how the space and time aligned data table is completed through processing the space-resolved drivers from their respective source coordinate representations into an intermediary coordinate representation shared with the responses and time-resolved drivers. The method shown in FIG. 11 applies to the items shown as 1141 in FIG. 1, and module 0430 incl. steps 0431, 0433 and 0432 in FIG. 4. The method itself consists of four main modules, to access the input data and intermediary quantities 1110, to derive the influence function and influence weights of the responses 1120, to combine the influence weights of the responses with the space-resolved drivers 1130, and to store the results and thus complete the space and time aligned data table 1140. Steps 1110 to 1140 below provide details of step 0132 in FIG. 1.

Further referring to FIG. 11, in module 1110 the method commences with step 1111 to access the wind direction from step 0421 in FIG. 4 and the turbulence statistics from step 0422 in FIG. 4. The module continues with step 1112 to access the responses in Lagrangian coordinate representation ($R_L$) from step 0422 in FIG. 4, then step 1113 to access the time-resolved drivers in Lagrangian coordinate representation ($DT_L$) from step 0421 in FIG. 4, and step 1114 to access the space-resolved driver input data in Eulerian coordinate representation ($DS_E$) and space resolution as specified by the user in step 0411 in FIG. 4 from step 0414 in FIG. 4.

Further referring to FIG. 11, module 1120 commences with step 0203 to derive the continuous influence function of the responses $R_L$. Informing existing mathematical models (numerical, analytical or parameterization solution of the advection-diffusion equation) with the wind direction and turbulence statistics from step 1111 yields the continuous influence function 0203 for a given time interval $T_1$. In step 1122 the continuous influence function is then discretized to a gridded Eulerian surface with a space resolution as specified by the user in step 0411 in FIG. 4. For each Eulerian surface grid cell this yields the corresponding surface influence weight $w(x,y,T_1)$ of the responses 0110.

Further referring to FIG. 11, module 1130 commences with accessing the space-resolved driver input data in Eulerian coordinate representation $DS_E$ from step 1114, here exemplified for two space-resolved drivers $DS_{E,1}(x,y)$ shown at 0121 in FIG. 1 and detailed at 1131 and $DS_{E,2}(x,y)$ shown at 0122 in FIG. 1 and detailed at 1132, such as land surface temperature and soil moisture. Additional examples for space-resolved driver input data include but are not limited to albedo, vegetation indices, land cover and topography. In step 1133 and step 1134 the two space-resolved drivers in Eulerian coordinate representation $DS_{E,1}(x,y)$ and $DS_{E,2}(x,y)$ are combined with the surface influence weights $w(x,y,T_1)$ of the responses from step 1122 above. This yields the two space-aggregated drivers $\overline{\overline{DS_{L,1}}}(x,y,T_1)$ shown at 1135 and $\overline{\overline{DS_{L,2}}}(x,y,T_1)$ shown at 1136 in the same Lagrangian coordinate representation as the responses, with double overbars indicating the space average.

Further referring to FIG. 11, in module 1140 the space-aggregated drivers $DS_{L,1}$ and $DS_{L,2}$ from steps 1135 and 1136 above are stored in the space and time aligned data table 1141 alongside the responses $R_L$ from step 1112 and the time resolved drivers $DT_{L,1}$ and $DT_{L,2}$ from step 1113, now all in the same Lagrangian coordinate representation. The method is then repeated for each $T_1$ thus completing the space and time aligned data table 1141. Finally, in step 1150 the space and time aligned data table is reported back to step 0441 in FIG. 4.

Further referring to FIG. 11, the above example illustrates the case of space-resolved driver input data that are static, i.e. not time-resolved. Analogously, if the driver input data is time-resolved and space-resolved such as frequently the case for satellite data and outputs from mathematical process models, the above method applies to each driver $DS_E(T_1)$, i.e. as a function of the time interval $T_1$. Furthermore, the provided example details responses $R_L$ at only one single location. Analogously, the method can be applied to responses in the same or different units at a multitude of locations in three-dimensional space $R_L(x,y,z)$. Also, the method is exemplified above for gridded space-resolved driver input data $DS_E$. Analogously, the continuous surface influence function can be combined directly with continuous space-resolved driver input data, such as vector images. Lastly, the above example details the case of creating the space and time aligned data table at 1141 from a space-aggregated, Lagrangian perspective. This is accomplished by using the surface influence weights $w(x,y,T_1)$ of the responses to perform the necessary Eulerian-to-Lagrangian convolution on the space-resolved drivers $DS_L$. This is the special case of the space-aligned time-series in step 0432 in FIG. 4. Analogously, the surface influence weights $w(x,y,T_1)$ can be combined with the space-aggregated responses $R_L(T_1)$ to yield the space-resolved, Eulerian perspective $R_L(x,y,T_1)$ of the time-aligned spatial grids in step 0433 in FIG. 4.

FIG. 12 illustrates how the driver-response relationship model is created. The method shown in FIG. 12 applies to the items shown as steps 0432, 0441, 0442 and 0450 in FIG. 4. The method itself consists of two main modules, to create the driver-response relationship model for the ceiling 1210 as shown in 0730 in FIGS. 7 and 0632 in FIG. 6, and to create the driver-response relationship model for the volume 1220 as shown in 0720 in FIGS. 7 and 0632 in FIG. 6. In module 1210 the method commences with the machine learning regression of responses at the ceiling $R_{L,c}$~$D_{L,c}$, yielding the driver-response relationship model at the ceiling $P_c(R_{L,c}, D_{L,c})$. In module 1220 the method completes with the machine learning regression of responses within the volume $R_{L,v}$~$D_{L,v}$ yielding the driver-response relationship model within the volume $P_v(R_{L,v}, D_{L,v})$. The above example illustrates the case for creating driver-response relationship models to provide the two terms relevant for solving the reduced flux conservation equation 0632 in FIG. 6. Analogously, the method can be used to create different driver-response relationship models to solve different physical constraints.

Figure 13:
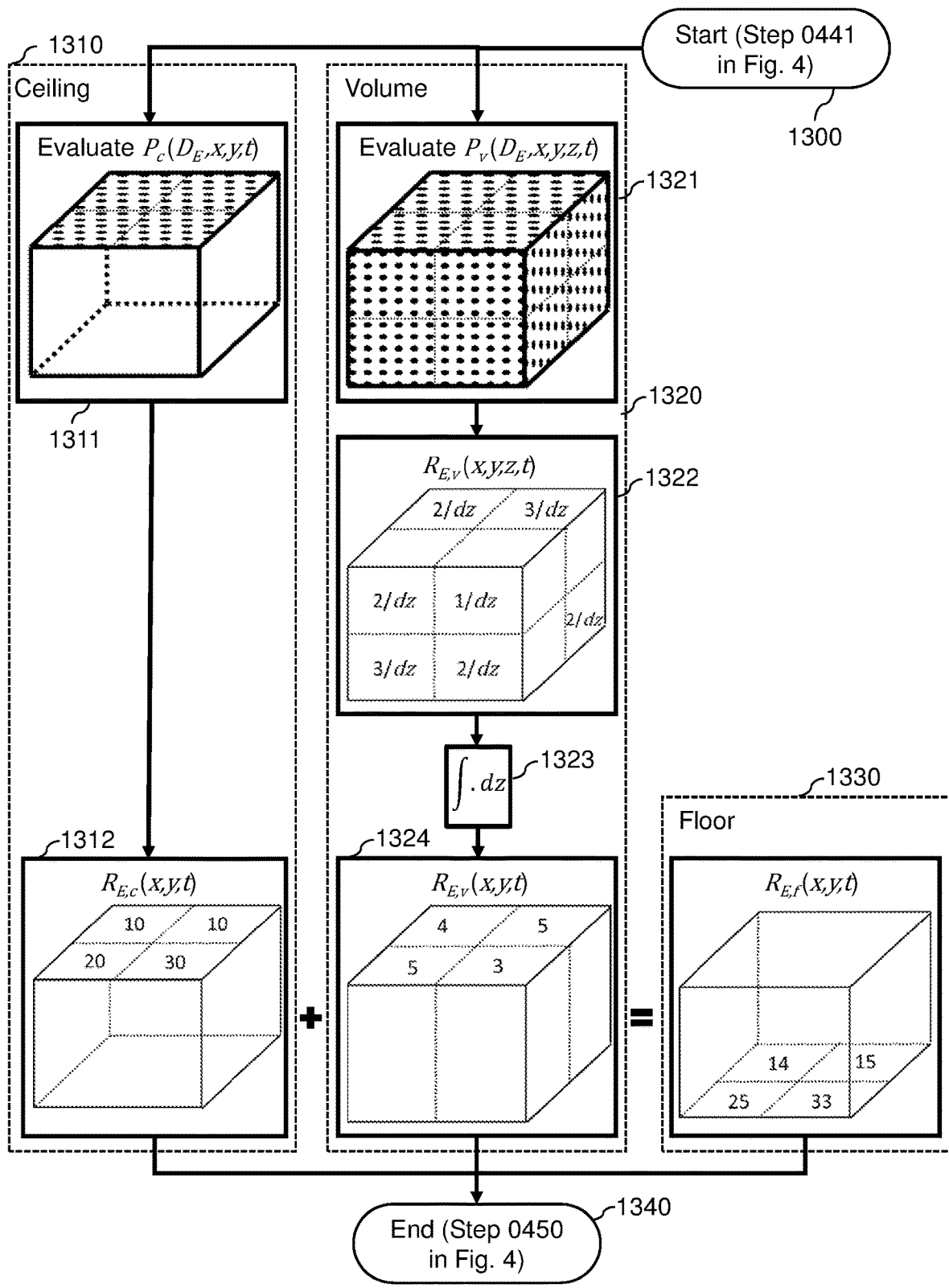
FIG. 13 shows how the driver-response relationship models shown in FIG. 12 are evaluated in conjunction with a physical constraint.

FIG. 13 illustrates how the driver-response relationship models, here 1212 in FIGS. 12 and 1222 in FIG. 12, are evaluated in conjunction with a physical constraint, here the reduced flux conservation equation 0632 in FIG. 6. The method shown in FIG. 12 applies to the items shown as steps 0441, 0442 and 0450 in FIG. 4. The method itself consists of three main modules, to evaluate the driver-response relationship model for the ceiling 1310 as shown at 0151 in FIG. 1, in 0730 in FIGS. 7 and 0632 in FIG. 6, to evaluate the driver-response relationship model for the volume 1320 as shown 0151 in FIG. 1, 0720 in FIGS. 7 and 0632 in FIG. 6, and to determine the flux from the floor 1330, which is also shown at 1130 in FIG. 1 and at 710 in FIGS. 7 and 0632 in FIG. 6.

Further referring to FIG. 13, in module 1310 the method commences with evaluating the driver-response relationship model for the ceiling $P_c(D_E,x,y,t)$ for all space-resolved and time-resolved drivers $D_E$ 1311. This yields the flux through the ceiling as shown in 0730 in FIG. 7, i.e. specifically the space-resolved and time-resolved responses 1312 in the coordinate representation space resolution and time resolution of the drivers as shown in 0631 in FIG. 6.

Further referring to FIG. 13, in module 1320 the method continuous with evaluating the driver-response relationship model for the volume $P_v(D_E,x,y,Z,t)$ for all space-resolved and time-resolved drivers $D_E$ 1321. This yields the flux per vertical increment dz which is the volume accumulation as shown in 0720 in FIG. 6, i.e. specifically the space-resolved and time-resolved responses 1322 in the coordinate representation, space resolution and time resolution of the drivers as shown in 0631 in FIG. 7. Following the physical constraint 0632 in FIG. 7, subsequent vertical integration 1323 transforms the volume responses into the same coordinate representation, space resolution, time resolution and unit 1324 as the ceiling responses 1312.

Further referring to FIG. 13, completing the physical constraint 0632 in FIG. 6 by adding ceiling responses and volume responses yields the flux from the floor 1330, also shown in FIG. 1 and FIG. 6. This completes the method by which the two remaining differential equation terms in the physical constraint in 0631 in FIG. 6 become fully quantifiable, thus exemplifying how output data performance is improved through combining physical constraints and data science principles, as well as combining complementary information from space-resolved input data and time-resolved input data. The above example illustrates the case for creating driver-response relationship models to provide the two terms relevant for solving the reduced flux conservation equation 0632 in FIG. 6. Analogously, the method can be used to create different driver-response relationship models to solve different physical constraints.

Figure 14:
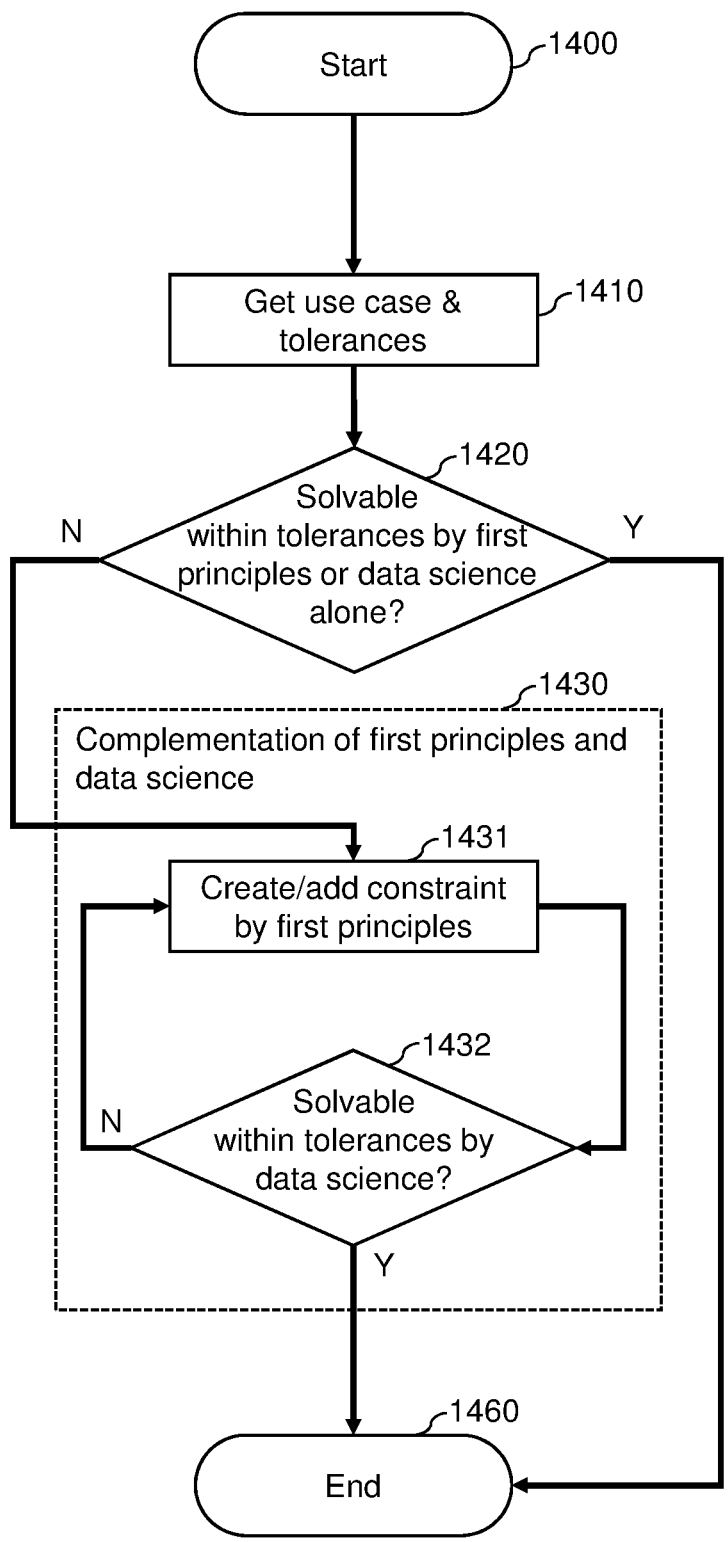
FIG. 14 shows how the physical constraints from the laws of science and data science principles can be used in conjunction with embodiments of the invention disclosed herein.

FIG. 14 illustrates how physical constraints from laws of science and data science principles complement each other in the systems and methods disclosed here, to systematically explore the natural and anthropogenic environment and generate new laws of science. The method described in FIG. 14 commences with obtaining a use case and corresponding tolerances on the solution 1410. It then inquires whether a use case is solvable within the provided tolerances either by physical constraints or data science principles alone 1420. If the use case is solvable within tolerances either by physical constraints or data science principles alone, the method ends here. Otherwise, the method continues with module 1430, which complements the properties of physical constraints and data science in an iterative fashion. Specifically, initial physical constraints 1431 are created from first principles, such as 0632 in FIG. 6. Data science 1432 is then used to solve the unknown terms in the physical constraints 1431 through extracting reciprocal information, such as through the method shown in FIG. 4, from data such as in 0110 in FIGS. 1 and 0120 in FIG. 1 or independent computer simulations, and if successful the methods ends here 1460. If the use case is not solvable within tolerances in the first iteration, the method continues to iterate by adding further constraints through first principles 1431 and/or by providing additional data sources to the data science solver 1432. The method ends 1460 once the use case is solved within tolerances or another cutoff criterion is reached.

4. Additional Embodiments and Variations

In one embodiment the systems and methods that have been described can be used for mitigating emissions from industrial leaks, such as natural gas leaks occurring during oil and gas extraction and delivery, power generation and general production. In this case the environmental response input data could be methane emissions, which is a type of mass flux. The first environmental driver input data could be information on production buildings and transportation networks, which is a type of anthropogenic infrastructure, as well as being a type of land use data. The second environmental driver input data could be information on the occurrence of methane in the natural environment, which is a type of geologic data.

In another embodiment the systems and methods that have been described can be used for characterizing and monitoring emissions, and validating emission inventories for agriculture, livestock, vehicular transportation, domestic heating and other sectors of anthropogenic activity. In this case the environmental response input data could be volatile organic compound emissions, which is a type of mass flux. The first environmental driver input data could be information on anthropogenic infrastructure. The second environmental driver input data could be information on volatile organic compound concentration, which is a type of scalar concentration data.

In another embodiment the systems and methods that have been described can be used for air quality control. In this case the environmental response input data could be particle flux data. The first environmental driver input data could be information on anthropogenic infrastructure. The second environmental driver input data could be particle count data.

In another embodiment the systems and methods that have been described can be used for urban heat control. In this case the environmental response input data could be energy flux data. The first environmental driver input data could be information on temperature. The second environmental driver input data could be information on radiation.

In another embodiment the systems and methods that have been described can be used for precision agriculture including to control crop intensity, irrigation and fertilization. In this case the environmental response input data could be $N_2O$ emissions, which is a type of mass flux. The first environmental driver input data could be information on land use. The second environmental driver input data could be information on scalar concentration.

In another embodiment the systems and methods that have been described can be used for quantifying natural emissions and water management, such as atmospheric water loss from inland waters incl. lakes and reservoirs. In this case the environmental response input data could be $H_2O$ (water vapor) emissions, which is a type of mass flux. The first environmental driver input data could be information on land use. The second environmental driver input data could be information on humidity.

In another embodiment the systems and methods that have been described can be used for controlling renewable energy production, such as for solar parks and wind farms. In this case the environmental response input data could be momentum flux data. The first environmental driver input data could be information on land use. The second environmental driver input data could be information on wind data.

The alternative features and configurations described in this document can be combined in any way capable of being understood by anyone skilled in the art. A number of variations and modifications of the disclosed embodiments can also be used. While the principles of the disclosure have been described above in connection with specific apparatuses and methods, it is to be clearly understood that this description is made only by way of example and not as limitation on the scope of the disclosure.

What is claimed is:

1. A method for generating enhanced measurements of an environment for control purposes, the method comprising the steps of:

receiving, in a processor, environmental response input data at a plurality of times, wherein the environmental response input data comprises data related to a natural environment, an anthropogenic environment, or a combination of the natural environment and the anthropogenic environment, and the environmental response input data is selected from the group of:
momentum flux data;
energy flux data;
mass flux data;
particle flux data;
liquid fluid flux data;
magnetic flux data;
electric flux data;

luminous flux data;
diffusion flux data;
volumetric flux data; and
acoustic flux data;
receiving, in the processor, first environmental driver input data at a plurality of times, wherein:
the first environmental driver input data comprises data related to the natural environment, the anthropogenic environment, or the combination of the natural environment and the anthropogenic environment;
the first environmental driver input data at least partially overlap the environmental response input data in space and time;
the first environmental driver input data is at least partially independent of the environmental response input data;
the first environmental driver input data is selected from the group of:
flux data, wherein the first environmental driver input flux data comprises a flux type that is different from the type of flux corresponding to the environmental response input flux data;
temperature data;
humidity data;
radiation data;
albedo data;
vegetation data;
land cover data;
land use data;
topography data;
geologic data;
wind data;
scalar concentration data;
particle count data; and
particle size distribution data;
receiving, in the processor, second environmental driver input data from a plurality of locations, wherein:
the second environmental driver input data comprises data related to the natural environment, the anthropogenic environment, or the combination of the natural environment and the anthropogenic environment;
the second environmental driver input data at least partially overlap the environmental response input data in space and time;
the second environmental driver input data is:
at least partially independent of the environmental response input data; and
at least partially independent of the first environmental driver input data;
the second environmental driver input data is selected from the group of:
flux data, wherein the second environmental driver input flux data comprises a flux type that is different from:
the type of flux corresponding to the environmental response input flux data; and
the type of flux corresponding to the first environmental driver input flux data;
temperature data;
humidity data;
radiation data;
albedo data;
vegetation data;
land cover data;
land use data;
geologic data;
topography data;
wind data;
scalar concentration data;
particle count data; and
particle size distribution data;
combining, in the processor, the environmental response input data, the first environmental driver input data, and the second environmental driver input data into a space and time aligned data table that comprises:
information from the environmental response input data;
information from the first environmental driver input data; and
information from the second environmental driver input data;
generating, in the processor, a driver-response relationship model in response to the space and time aligned data table;
applying, in the processor, the driver-response relationship model to the first environmental driver input data and the second environmental driver input data to produce environmental response output data wherein:
the environmental response output data is responsive to the driver response relationship model;
the environmental response output data has been enhanced from the environmental response input data in at least one of the following ways:
the environmental response output data has improved accuracy of a measurement;
the environmental response output data has improved precision of a measurement;
the environmental response output data comprises a greater time resolution;
the environmental response output data comprises a greater space resolution;
the environmental response output data comprises a higher time coverage; and
the environmental response output data comprises a higher spatial coverage; and
controlling an industrial leak using the environmental response output data.

2. The method of claim 1 wherein:
generating the driver-response relationship model is responsive to an analysis selected from the group of:
a conservation of mass analysis;
a conservation of linear momentum analysis;
a conservation of angular momentum analysis;
a conservation of energy analysis;
a diffusion analysis;
a fluid flow analysis;
a viscosity analysis;
a conduction analysis;
a flux-gradient analysis;
a flux-variance analysis;
an advection analysis;
a dispersion analysis;
a resistance analysis;
an evapotranspiration analysis;
a reactive decay analysis; and
a closure analysis.

3. The method of claim 1 wherein:
receiving the environmental response input data further comprises receiving the environmental response input data from a plurality of locations.

4. The method of claim 1 wherein:
receiving the first environmental driver input data further comprises receiving the first environmental driver input data from a plurality of locations.

5. The method of claim 1 wherein:
receiving second environmental driver input data further comprises receiving the second environmental driver input data at a plurality of times.

6. The method of claim 1 wherein:
the environmental response input data comprises mass flux data; and the
first environmental driver input data comprises land use data.

7. The method of claim 1 wherein:
the environmental response input data comprises energy flux data.

8. The system of claim 1 wherein:
the higher spatial coverage extends over a broader range of locations.

9. The system of claim 1 wherein:
the higher time coverage extends over a broader range of times.

10. A system for generating enhanced measurements of an environment for control purposes, the system comprising a processor, wherein:
the processor is configured for receiving environmental response input data at a plurality of times, wherein the environmental response input data comprises data related to a natural environment, an anthropogenic environment, or a combination of a natural environment and an anthropogenic environment and the environmental response input data is selected from the group of:
momentum flux data;
energy flux data;
mass flux data;
particle flux data;
liquid fluid flux data;
magnetic flux data;
electric flux data;
luminous flux data;
diffusion flux data;
volumetric flux data; and
acoustic flux data;
the processor is configured for receiving first environmental driver input data at a plurality of times, wherein;
the first environmental driver input data comprises data related to the natural environment, the anthropogenic environment; or the combination of the natural environment and the anthropogenic environment;
the first environmental driver input data at least partially overlap the environmental response input data in space and time;
the first environmental driver input data is at least partially independent of the environmental response input data;
the first environmental driver input data is selected from the group of:
flux data, wherein the first environmental driver input flux data comprises a flux type that is different from the type of flux corresponding to the environmental response input flux data;
temperature data;
humidity data;
radiation data;
albedo data;
vegetation data;
land cover data;
land use data;
topography data;
geologic data;
wind data;
scalar concentration data;
particle count data; and
particle size distribution data;
the processor is configured for receiving second environmental driver input data from a plurality of locations, wherein:
the second environmental driver input data comprises data related to the natural environment, the anthropogenic environment, or the combination of the natural environment and the anthropogenic environment;
the second environmental driver input data at least partially overlap the environmental response input data in space and time;
the second environmental driver input data is:
at least partially independent of the environmental response input data; and
at least partially independent of the first environmental driver input data;
the second environmental driver input data is selected from the group of:
flux data, wherein the second environmental driver input flux data comprises a flux type that is different from:
the type of flux corresponding to the environmental response input flux data; and
the type of flux corresponding to the first environmental driver input flux data;
temperature data;
humidity data;
radiation data;
albedo data;
vegetation data;
land cover data;
land use data;
topography data;
geologic data;
wind data;
scalar concentration data;
particle count data; and
particle size distribution data;
the processor is configured for combining the environmental response input data, the first environmental driver input data, and the second environmental driver input data into a space and time aligned data table that comprises:
information from the environmental response input data;
information from the first environmental response driver input data; and information from the second environmental response driver input data;
the processor is configured for generating-a driver-response relationship model in response to the space and time aligned data table;
the processor is configured for applying the driver-response relationship model to the first environmental driver data and the second environmental driver data to produce environmental response output data wherein:
the environmental response output data is responsive to the driver response relationship model;

the environmental response output data has been enhanced from the environmental response input data in at least one of the following ways:
the environmental response output data has improved accuracy of a measurement;
the environmental response output data has improved precision of a measurement;
the environmental response output data comprises a greater time resolution;
the environmental response output data comprises a greater space resolution;
the environmental response output data comprises a higher time coverage; and
the environmental response output data comprises a higher spatial coverage; and
the system controls an industrial leak in response to the environmental response output data.

11. The system of claim 10 wherein:
receiving the environmental response input data further comprises receiving the environmental response input data from a plurality of locations.

12. The system of claim 10 wherein:
receiving the first environmental driver input data further comprises receiving the first environmental driver input data from a plurality of locations.

13. The system of claim 10 wherein:
receiving second environmental driver input data further comprises receiving the second environmental driver input data at a plurality of times.

14. The system of claim 10, wherein:
the system is configured for air quality control.

15. A system for generating enhanced measurements of an environment for control purposes, the system comprising:
a computer-readable memory wherein said memory is located in a computing device;
a computer program stored in the computer-readable memory and adapted to be executed on a processor wherein the computer program is configured for:
receiving environmental response input data at a plurality of times, wherein the environmental response input data comprises data related to a natural environment, an anthropogenic environment, or a combination of the natural environment and the anthropogenic environment and the environmental response input data is selected from the group of:
momentum flux data;
energy flux data;
mass flux data;
particle flux data;
liquid fluid flux data;
magnetic flux data;
electric flux data;
luminous flux data;
diffusion flux data;
volumetric flux data; and
acoustic flux data;
receiving first environmental driver input data at a plurality of times, wherein:
the first environmental driver input data comprises data related to the natural environment, the anthropogenic environment, or a combination of the natural environment and the anthropogenic environment;
the first environmental driver input data at least partially overlap the environmental response input data in space and time;
the first environmental driver input data is at least partially independent of the environmental response input data;
the first environmental driver input data is selected from the group of:
flux data, wherein the first environmental driver input flux data comprises a flux type that is different from the type of flux corresponding to the environmental response input flux data;
temperature data;
humidity data;
radiation data;
albedo data;
vegetation data;
land cover data;
land use data;
topography data;
geologic data;
wind data;
scalar concentration data;
particle count data; and
particle size distribution data;
receiving second environmental driver input data from a plurality of locations, wherein:
the second environmental driver input data comprises data related to the natural environment, the anthropogenic environment, or a combination of the natural environment and the anthropogenic environment;
the second environmental driver input data at least partially overlap the environmental response input data in space and time;
the second environmental driver input data is:
at least partially independent of the environmental response input data; and
at least partially independent of the first environmental driver input data;
the second environmental driver input data is selected from the group of:
flux data, wherein the second environmental driver input flux data comprises a flux type that is different from:
the type of flux corresponding to the environmental response input flux data; and
the type of flux corresponding to the first environmental driver input flux data;
temperature data;
humidity data;
radiation data;
albedo data;
vegetation data;
land cover data;
land use data;
topography data;
geologic data;
wind data;
scalar concentration data;
particle count data; and
particle size distribution data;
combining the environmental response input data, the first environmental driver input data, and the second environmental driver input data into a space and time aligned data table that comprises:
information from the environmental response input data;

information from the first environmental response driver input data; and information from the second environmental response driver input data;

generating a driver-response relationship model in response to the space and time aligned data table;

applying the driver-response relationship model to the first environmental driver data and the second environmental driver data to produce environmental response output data that has been enhanced from the environmental response input data in at least one of the following ways:
- the environmental response output data has improved accuracy of a measurement;
- the environmental response output data has improved precision of a measurement;
- the environmental response output data comprises a greater time resolution;
- the environmental response output data comprises a greater space resolution;
- the environmental response output data comprises a higher time coverage; and
- the environmental response output data comprises a higher spatial coverage; and controlling an industrial leak in response to the environmental response output data.

16. The system of claim 15 wherein:

generating the driver-response relationship model is responsive to an analysis selected from the group of:
- a conservation of mass analysis;
- a conservation of linear momentum analysis;
- a conservation of angular momentum analysis;
- a conservation of energy analysis;
- a diffusion analysis;
- a fluid flow analysis;
- a viscosity analysis;
- a conduction analysis;
- a flux-gradient analysis;
- a flux-variance analysis;
- an advection analysis;
- a dispersion analysis;
- a resistance analysis;
- an evapotranspiration analysis;
- a reactive decay analysis; and
- a closure analysis.

* * * * *